US006784174B1

(12) United States Patent
Cumming

(10) Patent No.: US 6,784,174 B1
(45) Date of Patent: Aug. 31, 2004

(54) PYRIDINE AND PYRIMIDINE DERIVATIVES AND THEIR USE AS INHIBITORS OF CYTOKINE MEDIATED DISEASE

(75) Inventor: John G Cumming, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/937,018

(22) PCT Filed: Mar. 17, 2000

(86) PCT No.: PCT/GB00/01006

§ 371 (c)(1), (2), (4) Date: Sep. 20, 2001

(87) PCT Pub. No.: WO00/56738

PCT Pub. Date: Sep. 28, 2000

(30) Foreign Application Priority Data

Mar. 23, 1999 (GB) .......................................... 9906566

(51) Int. Cl.[7] .................... C07D 495/04; C07D 513/04; C07D 471/04; A61K 31/33

(52) U.S. Cl. ............................... 514/234.2; 514/260.1; 514/262.1; 514/263.4; 514/264.11; 544/117; 544/118; 544/258; 544/262; 544/277; 544/278; 544/279; 544/280

(58) Field of Search ................................ 544/117, 118, 544/258, 262, 278, 277, 279, 280; 514/234.2, 260.1, 262.1, 263.4, 264.11

(56) References Cited

U.S. PATENT DOCUMENTS

| | | | | |
|---|---|---|---|---|
| 3,211,555 | A | 10/1965 | Mory et al. | 96/99 |
| 3,755,332 | A | 8/1973 | Wasley et al. | 260/288 R |
| 6,432,949 | B1 | 8/2002 | Brown et al. | 564/157 |
| 6,455,520 | B1 | 9/2002 | Brown et al. | 514/232.2 |
| 6,465,455 | B1 | 10/2002 | Brown et al. | 514/231.2 |
| 6,498,274 | B1 | 12/2002 | Brown et al. | 564/157 |

FOREIGN PATENT DOCUMENTS

| | | |
|---|---|---|
| EP | 447891 | * 9/1991 |
| EP | 0 635 507 | 1/1995 |
| WO | WO 95/19774 | 7/1995 |
| WO | WO 96/40706 | * 12/1996 |
| WO | WO 97/13771 | 4/1997 |
| WO | 98/22103 | 5/1998 |
| WO | 99/15164 | 4/1999 |
| WO | 99/59959 | 11/1999 |
| WO | 00/07980 | 2/2000 |
| WO | 00/07991 | 2/2000 |
| WO | 00/20402 | 4/2000 |
| WO | 00/55120 | 9/2000 |
| WO | 00/55153 | 9/2000 |
| WO | 01/27089 | 4/2001 |

OTHER PUBLICATIONS

Thompson et al., Tyrosine Kinase Inhibitors, J. Med. Chem., vol. 38, No. 19, pp. 3780–3788, 1995.*

Thompson A M et al: "Tyrosine Kinase Inhibitors. 7. 7–Amino–4–(Phenylamino–) and 7–Amino–4–((Phenylmethyl) Amino'4, 3–d! Pyrimidines: A New Class of Inhibitors of the Tyrosine Kinase Activity of the Epidermal Growth Factor Receptor" Journal of Medicinal Chemistry, US, American Chemical Society Washington, vol. 38, No. 19, 1995, pp. 3780–3788, XP002140323, ISSN:0022–2623 cited in the application p. 3780, paragraph 1; example 7Z; table 1.

Myers M R et al: "The preparation and SARof 4–(anilino), 4–(phenoxy), and 4–(thiophenoxy)–quinazolines: inhibitors of p56 and EGF–R tyrosine kinase activity" Bioorganic & Medicinal Chemistry Letters,GB, Oxford, vol. 7, No. 4, Feb. 18, 1997, pp. 417–420, XP004136037 ISSN:0960–894X, p. 417, paragraph 1; table 1.

Kelley J L et al: Journal of Medicinal Chemistry, US, American Chemical Society. Washington, vol. 33, No. 5, 1990, pp. 1360–1363, XP002140324 ISSN: 0022–2623 the whole document.

Hanson, "Review—Pulmonary–Allergy, Dermatological, Gastrointestinal & Arthritis—Inhibitors of p38 kinase", Exp. Opin. Ther. Patents, 1997, XP–002086152, pp. 729–733.

* cited by examiner

*Primary Examiner*—Deepak Rao
(74) *Attorney, Agent, or Firm*—Morgan, Lewis & Bockius LLP

(57) ABSTRACT

This invention concerns a bicyclic compound of Formula (I), wherein: G is N, CH or C(CN); ring X is a 5- or 6-membered fused heteroaryl ring which contains 1, 2, or 3 heteroatoms selected from oxygen, sulphur and nitrogen; m is 0–2; $R^1$ is a group such as hydroxy, halo, trifluoromethyl, cyano, mercapto, nitro, amino, carboxy and carbamoyl; each of $R^2$ and $R^3$ is hydrogen, halo, $C_{1-6}$alkyl, $C_{2-6}$alkenyl or $C_{2-6}$ alkynyl; $R^4$ is a group such as hydrogen, hydroxy, $C_{1-6}$alkyl, $C_{1-6}$alkoxy, amino and N-$C_{1-6}$alkylamino; $R^5$ is a group such as hydrogen, halo, trifluoromethyl, cyano, nitro, amino and hydroxy, and q is 0–4; or a pharmaceutically acceptable salt or an in vivo cleavable ester thereof; processes for its preparation, a pharmaceutical composition containing it and its use in the treatment of diseases or medical conditions mediated by cytokines.

(I)

13 Claims, No Drawings

PYRIDINE AND PYRIMIDINE DERIVATIVES AND THEIR USE AS INHIBITORS OF CYTOKINE MEDIATED DISEASE

This application is the National Phase of International Application PCT/GB00/01006 filed Mar. 17, 2000 which designated the U.S. and International Application was published under PCT Article 21(2) in English.

This invention concerns certain amide derivatives and their use as inhibitors of cytokine mediated disease. The invention also concerns processes for the manufacture of said novel amide derivatives, pharmaceutical compositions containing them and their use in therapeutic methods, for example by virtue of inhibition of cytokine mediated disease.

The amide derivatives disclosed in the present invention are inhibitors of the production of cytokines such as Tumour Necrosis Factor (hereinafter TNF), for example TNFα, and various members of the interleukin (hereinafter IL) family, for example IL-1, IL-6 and IL-8. Accordingly the compounds of the invention will be useful in the treatment of diseases or medical conditions in which excessive production of cytokines occurs, for example excessive production of TNFα or IL-1. It is known that cytokines are produced by a wide variety of cells such as monocytes and macrophages and that they give rise to a variety of physiological effects which are believed to be important in disease or medical conditions such as inflammation and immunoregulation. For example, TNFα and IL-1have been implicated in the cell signalling cascade which is believed to contribute to the pathology of disease states such as inflammatory and allergic diseases and cytokine-induced toxicity. It is also known that, in certain cellular systems, TNFα production precedes and mediates the production of other cytokines such as IL-1.

Abnormal levels of cytokines have also been implicated in, for example, the production of physiologically-active eicosanoids such as the prostaglandins and leukotrienes, the stimulation of the release of proteolytic enzymes such as collagenase, the activation of the immune system, for example by stimulation of T-helper cells, the activation of osteoclast activity leading to the resorption of calcium, the stimulation of the release of proteoglycans from, for example, cartilage, the stimulation of cell proliferation and to angiogenesis.

Cytokines are also believed to be implicated in the production and development of disease states such as inflammatory and allergic diseases, for example inflammation of the joints (especially rheumatoid arthritis, osteoarthritis and gout), inflammation of the gastrointestinal tract (especially inflammatory bowel disease, ulcerative colitis, Crohn's disease and gastritis), skin disease (especially psoriasis, eczema and dermatitis) and respiratory disease (especially asthma, bronchitis, allergic rhinitis, adult respiratory distress syndrome and chronic obstructive pulmonary disease), and in the production and development of various cardiovascular and cerebrovascular disorders such as congestive heart disease, myocardial infarction, the formation of atherosclerotic plaques, hypertension, platelet aggregation, angina, stroke, Alzheimer's disease, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoporosis and periodontitis, and the abnormal changes in bone metabolism which may accompany rheumatoid arthritis and osteoarthritis. Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke. Excessive cytokine production has also been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis.

Evidence of the central role played by TNFα in the cell signalling cascade which gives rise to rheumatoid arthritis is provided by the efficacy in clinical studies of antibodies of TNFα (*The Lancet*, 1994, 34, 1125 and *British Journal of Rheumatology*, 1995, 34, 334).

Thus cytokines such as TNFα and IL-1 are believed to be important mediators of a considerable range of diseases and medical conditions. Accordingly it is expected that inhibition of the production of and/or effects of these cytokines will be of benefit in the prophylaxis, control or treatment of such diseases and medical conditions.

Without wishing to imply that the compounds disclosed in the present invention possess pharmacological activity only by virtue of an effect on a single biological process, it is believed that the compounds inhibit the effects of cytokines by virtue of inhibition of the enzyme p38 kinase. p38 kinase, otherwise known as cytokine suppressive binding protein (hereinafter CSBP) and reactivating kinase (hereinafter RK), is a member of the mitogen-activated protein (hereinafter MAP) kinase family of enzymes which is known to be activated by physiological stress such as that induced by ionising radiation, cytotoxic agents, and toxins, for example endotoxins such as bacterial lipopolysaccharide, and by a variety of agents such as the cytokines, for example TNFα and IL-1. It is known that p38 kinase phosphorylates certain intracellular proteins which are involved in the cascade of enzymatic steps which leads to the biosynthesis and excretion of cytokines such as TNFα and IL-1. Known inhibitors of p38 kinase have been reviewed by G J Hanson in *Expert Opinions on Therapeutic Patents*, 1997, 7, 729–733. p38 kinase is known to exist in isoforms identified as p38α and p38β.

The compounds disclosed in the present invention are inhibitors of the production of cytokines such as TNF, in particular of TNFα, and various interleukins, in particular IL-1.

It is disclosed in *J. Medicinal Chemistry*, 1995, 38, 3780–3788, that certain 4-anilinopyrido[4,3-d]pyrimidines are inhibitors of the tyrosine kinase activity of the epidermal growth factor receptor. One of the compounds disclosed therein is 7-amino-4-(3-acetamidoanilino)pyrido[4,3-d]pyrimidine.

Accordingly the present invention provides a bicyclic compound of the Formula (I):

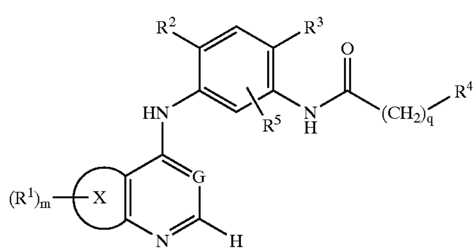

wherein:

G is N, CH or C(CN);

ring X is a 5- or 6-membered fused heteroaryl ring which contains 1, 2 or 3 heteroatoms selected from oxygen, sulphur and nitrogen;

m is 0, 1 or 2;

$R^1$ is hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O—($C_{1-3}$alkyl)-O—. $C_{1-6}$alkylS(O)$_n$— (wherein n is 0–2), N-$C_{1-6}$alkylamino, N,N-($C_{1-6}$alkyl)$_2$amino, $C_{1-6}$alkoxycarbonyl, N-$C_{1-6}$alkylcarbamoyl, N,N-($C_{1-6}$ alkyl)$_2$carbamoyl, $C_{2-6}$alkanoyl, $C_{1-6}$alkanoyloxy, $C_{1-6}$alkanoylamino, N-$C_{1-6}$alkylsulphamoyl, N,N-($C_{1-6}$ alkyl)$_2$sulphamoyl, $C_{1-6}$alkylsulphonylamino, $C_{1-6}$alkylsulphonyl-N-($C_{1-6}$alkyl)amino, or $R^1$ is of the Formula (IA):

A—$(CH_2)_p$—B— (IA)

wherein A is halo, hydroxy, $C_{1-6}$alkoxy, $C_{1-6}$alkylS(O)$_n$— (wherein n is 0–2), cyano, amino, N-$C_{1-6}$alkylamino, N,N-($C_{1-6}$alkyl)$_2$amino, carboxy, $C_{1-6}$alkoxycarbonyl, carbamoyl, N-$C_{1-6}$alkylcarbamoyl or N,N-($C_{1-6}$alkyl)$_2$ carbamoyl, p is 1–6, and B is a bond, oxy, imino, N-($C_{1-6}$alkyl)imino or —C(O)NH—, with the proviso that p is 2 or more unless B is a bond or —C(O)NH—, or $R^1$ is of the Formula (IB):

D—E— (IB)

wherein D is aryl, heteroaryl or heterocyclyl and E is a bond, $C_{1-6}$alkylene, $C_{1-6}$alkyleneoxy, oxy, imino, N-($C_{1-6}$alkyl)imino, $C_{1-6}$alkyleneimino, N-($C_{1-6}$alkyl)-$C_{1-6}$alkyleneimino, $C_{1-6}$alkyleneoxy-$C_{1-6}$alkylene, $C_{1-6}$alkyleneimino-$C_{1-6}$alkylene, N-($C_{1-6}$alkyl)-$C_{1-6}$ alkyleneimino-$C_{1-6}$alkylene, —C(O)NH—, —$SO_2$NH—, —NH$SO_2$— or $C_{2-6}$alkanoylimino, and any aryl, heteroaryl or heterocyclyl group in a $R^1$ group may be optionally substituted with one or more groups selected from hydroxy, halo, $C_{1-6}$alkyl, $C_{1-6}$alkoxy, carboxy, $C_{1-6}$alkoxycarbonyl, carbamoyl, N-$C_{1-6}$ alkylcarbamoyl, N-($C_{1-6}$alkyl)$_2$carbamoyl, $C_{2-6}$alkanoyl, amino, N-$C_{1-6}$alkylamino and N,N-($C_{1-6}$ alkyl)$_2$amino, and any heterocyclyl group in a $R^1$ group may be optionally substituted with one or two oxo or thioxo substituents, and any of the $R^1$ groups defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, $C_{1-6}$alkoxy, N-$C_{1-6}$alkylamino, N,N-($C_{1-6}$alkyl)$_2$amino and heterocyclyl;

$R^2$ is hydrogen, halo, $C_{1-6}$alkyl, $C_{2-6}$alkenyl or $C_{2-6}$alkynyl;

$R^3$ is hydrogen, halo, $C_{1-6}$alkyl, $C_{2-6}$alkenyl or $C_{2-6}$alkynyl, $R^4$ is hydrogen, hydroxy, $C_{1-6}$alkyl, $C_{1-6}$alkoxy, amino, N-$C_{1-6}$alkylamino, N,N-($C_{1-6}$alkyl)$_2$amino, hydroxy$C_{2-6}$alkoxy, $C_{1-6}$alkoxy$C_{2-6}$alkoxy, amino$C_{2-6}$ alkoxy, N-$C_{1-6}$alkylamino$C_{3-6}$alkoxy, N,N-($C_{1-6}$alkyl)$_2$ amino$C_{2-6}$alkoxy or $C_{3-7}$cycloalkyl, or $R^4$ is of the Formula (IC):

—K—J (IC)

wherein J is aryl, heteroaryl or heterocyclyl and K is a bond, oxy, imino, N-($C_{1-6}$alkyl)imino, oxy$C_{1-6}$ alkylene, imino$C_{1-6}$alkylene, N-($C_{1-6}$alkyl)imino$C_{1-6}$ alkylene, —NHC(O)—, —$SO_2$NH—, —NH$SO_2$— or —NHC(O)—$C_{1-6}$alkylene-, and any aryl, heteroaryl or heterocyclyl group in a $R^4$ group may be optionally substituted by one or more groups selected from hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O—($C_{1-3}$alkyl)-O—, $C_{1-6}$alkylS(O)$_n$— (wherein n is 0–2), N-$C_{1-6}$ alkylamino, N,N-($C_{1-6}$alkyl)$_2$amino, $C_{1-6}$alkoxycarbonyl, N-$C_{1-6}$alkylcarbamoyl, N,N-($C_{1-6}$ alkyl)$_2$carbamoyl, $C_{2-6}$alkanoyl, $C_{1-6}$alkanoyloxy, $C_{1-6}$alkanoylamino, N-$C_{1-6}$alkylsulphamoyl, N,N-($C_{1-6}$ alkyl)$_2$sulphamoyl, $C_{1-6}$alkylsulphonylamino and $C_{1-6}$alkylsulphonyl-N-($C_{1-6}$alkyl)amino, or any aryl, heteroaryl or heterocyclyl group in a $R^4$ group may be optionally substituted with one or more groups of the Formula (IA'):

$B^1$—$(CH_2)_p$—$A^1$ (IA')

wherein $A^1$ is halo, hydroxy, $C_{1-6}$alkoxy, cyano, amino, N-$C_{1-6}$alkylamino, N,N-($C_{1-6}$alkyl)$_2$amino, carboxy, $C_{1-6}$alkoxycarbonyl, carbamoyl, N-$C_{1-6}$ alkylcarbamoyl or N,N-($C_{1-6}$alkyl)$_2$carbamoyl, p is 1–6, and $B^1$ is a bond, oxy, imino, N-($C_{1-6}$alkyl)imino or —NHC(O)—, with the proviso that p is 2 or more unless $B^1$ is a bond or —NHC(O)—, or any aryl, heteroaryl or heterocyclyl group in a $R^4$ group may be optionally substituted with one or more groups of the Formula (IB'):

—$E^1$—$D^1$ (IB')

wherein $D^1$ is aryl, heteroaryl or heterocyclyl and $E^1$ is a bond, $C_{1-6}$alkylene, oxy$C_{1-6}$alkylene, oxy, imino, N-($C_{1-6}$alkyl)imino, imino$C_{1-6}$alkylene, N-($C_{1-6}$alkyl)-imino$C_{1-6}$alkylene, $C_{1-6}$alkylene-oxy$C_{1-6}$alkylene, $C_{1-6}$alkylene-imino$C_{1-6}$alkylene, $C_{1-6}$alkylene-N-($C_{1-6}$ alkyl)imino$C_{1-6}$alkylene, —NHC(O)—, —NH$SO_2$—, —$SO_2$NH— or —NHC(O)—$C_{1-6}$alkylene-, and any aryl, heteroaryl or heterocyclyl group in a substituent on $R^4$ may be optionally substituted with one or more groups selected from hydroxy, halo, $C_{1-6}$alkyl, $C_{1-6}$alkoxy, carboxy, $C_{1-6}$alkoxycarbonyl, carbamoyl, N-$C_{1-6}$alkylcarbamoyl, N-($C_{1-6}$alkyl)$_2$carbamoyl, $C_{2-6}$alkanoyl, amino, N-$C_{1-6}$alkylamino and N,N-($C_{1-6}$ alkyl)$_2$amino, and any $C_{3-7}$cycloalkyl or heterocyclyl group in a $R^4$ group may be optionally substituted with one or two oxo or thioxo substituents, and any of the $R^4$ groups defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, $C_{1-6}$alkoxy, N-$C_{1-6}$alkylamino, N,N-($C_{1-6}$alklyl)$_2$ amino and heterocyclyl;

$R^5$ is hydrogen, halo, trifluoromethyl, cyano, nitro, amino, hydroxy, $C_{1-6}$alkyl, $C_{2-6}$alkenyl, $C_{2-6}$alkynyl, $C_{1-6}$alkoxy, N-$C_{1-6}$alkylamino or N,N-($C_{1-6}$alkyl)$_2$ amino;

q is 0, 1, 2, 3 or 4;

or a pharmaceutically acceptable salt or an in vivo cleavable ester thereof;

with the proviso that 7-amino-4-(3-acetamidoanilino) pyrido[4,3-d]pyrimidine is excluded.

It is to be understood that the bicyclic ring within the compound of Formula (I) is shown with a hydrogen atom attached to the carbon between the N atom and G group in order to indicate that this position is unsubstituted. Thereby it is to be understood that that hydrogen atom may not be replaced by a $R^1$ substituent. It should also be understood however that when G is a CH group, that CH group may bear any one of the $R^1$ substituents.

It is to be understood that, insofar as certain of the compounds of the Formula (I) defined above may exist in optically active or racemic forms by virtue of one or more asymmetric carbon atoms, the invention includes in its definition any such optically active or racemic form which possesses the property of inhibiting cytokines, in particular TNF. The synthesis of optically active forms may be carried out by standard techniques of organic chemistry well known in the art, for example by synthesis from optically active starting materials or by resolution of a racemic form. Similarly, inhibitory properties against TNF may be evaluated using the standard laboratory techniques referred to hereinafter.

For the avoidance of doubt, it is to be understood that when, for example, $R^1$ is a group of the Formula (IB):

$$D—E— \qquad (IB)$$

and the linking group E is, for example, a $C_{1-6}$alkyleneoxy group such as —$CH_2CH_2O$—, it is a $CH_2$ group which is attached to D and the O atom which is attached to the bicyclic ring within Formula (I). Similarly when, for example, $R^4$ is a group of the Formula (IB'):

$$—E^1—D^1 \qquad (IB')$$

and the linking group $E^1$ is, for example, an imino$C_{1-6}$alkylene group such as —$NHCH_2CH_2$—, it is a $CH_2$ group which is attached to $D^1$ and the NH group which is attached to the bicyclic ring within Formula (I). An analogous convention applies to other bidentate linking groups.

In this specification the term "alkyl" includes both straight and branched chain alkyl groups but references to individual alkyl groups such as "propyl" are specific for the straight chain version only. For example, "$C_{1-6}$alklyl" includes propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "amino$C_{2-6}$alkoxy" includes 2-aminoethoxy, 2-aminopropoxy and 3-amino-2-methylpropoxy. The term "halo" refers to fluoro, chloro, bromo and iodo.

The term "aryl" refers to phenyl or naphthyl. When an $R^4$ group involves a $D^1$ group and $D^1$ is aryl, that "aryl" refers to phenyl, indenyl, indanyl, naphthyl, tetrahydronaphthyl or fluorenyl.

The term "heteroaryl" refers to, unless otherwise further specified, a monocyclic-, bicyclic- or tricyclic-5–14 membered ring that is unsaturated or partially unsaturated, with one to five ring heteroatoms selected from nitrogen, oxygen and sulphur, wherein a —$CH_2$-group can optionally be replaced by a —C(O)—, a ring nitrogen atom may optionally bear a $C_{1-6}$alkyl group or a ring nitrogen and/or ring sulphur atom may be optionally oxidised to form the N-oxide and/or the S-oxides. Examples of "heteroaryl" include thienyl, furyl, pyranyl, pyrrolyl, pyrazolinyl, imidazolyl, imidazolinyl, pyrazolyl, pyrazolinyl, thiazolyl, oxazolyl, isoxazolyl, pyridyl, pyridyl-N-oxide, oxopyridyl, oxoquinolyl, pyrimidinyl, pyrazinyl, oxopyrazinyl, pyridazinyl, indolyl, benzofuranyl, benzimidazolyl, benzothiazolyl, quinolyl, N-methyloxoquinolyl, isoquinolinyl, quinazolinyl, xanthenyl, quinoxalinyl, indazolyl, benzofuranyl, cinnolinolyl, carbazolyl, dibenzofuranyl, dibenzothiophenyl, S,S-dioxodibenzothiophenyl, dibenzo-1,4-dioxinyl, phenoxathiinyl, phenoxazinyl, dibenzothiinyl, phenothiazinyl, thianthrenyl, benzofuropyridyl, pyridoindolyl, acridinyl and phenanthridinyl. When an $R^4$ group involves a $D^1$ group and $D^1$ is heteroaryl, that "heteroaryl" preferably refers to furyl, thienyl, pyrrolyl, pyrrolinyl, oxazolyl, isoxazolyl, imidazolyl, imidazolinyl, pyrazolyl, pyrazolinyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl, or benzo derivatives such as 2,3-dihydrobenzofuranyl, 2,3-dihydrobenzothienyl, indolinyl, isoindolinyl, chromanyl and isochromanyl, more preferably that "heteroaryl" refers to furyl, thienyl, 3-pyrrolinyl, isoxazolyl, thiazolyl, pyridyl, benzothienyl, benzofurazanyl, quinolyl, carbazolyl, dibenzofuranyl or dibenzothiophenyl.

Ring X is a 5- or 6-membered fused heteroaryl ring which contains 1, 2 or 3 heteroatoms selected from oxygen, sulphur and nitrogen Suitably ring X is unsaturated or partially unsaturated wherein a —$CH_2$— group can optionally be replaced by a —C(O)—, a ring nitrogen atom may optionally bear a $C_{1-6}$alkyl group or a ring nitrogen and/or ring sulphur atom may be optionally oxidised to form the N-oxide and/or the S-oxides. Examples of the diradicals of suitable fused heteroaryl rings include thiendiyl, furandiyl, imidazolediyl, pyrazolediyl, oxazolediyl, isoxazolediyl, thiazolediyl, isothiazolediyl, 1,2,3-oxadiazolediyl, 1,2,3-triazolediyl, pyridinediyl, pyrimidinediyl, pyrazinedlyl, pyridazinediyl and 1,3,4-triazinediyl. Examples of the mono-radical of suitable bicyclic rings formed by the fusion of ring X to the adjacent nitrogen-containing 6-membered heteroaryl ring within Formula (I) include furopyridyl, furopyrimidinyl, thienopyridyl, thienopyrimidinyl, pyrrolopyridyl, pyrrolopyrimidinyl, pyrrolinopyridyl, pyrrolinopyrimidinyl, oxopyrrolinopyridyl, oxopyrrolinopyrimidinyl, oxazolopyridyl, oxazolopyrimidinyl, oxazolinopyridyl, oxazolinopyrimidinyl, oxooxazolinopyridyl, oxooxazolinopyrimidinyl, isoxazolopyridyl, isoxazolopyrimidinyl, thiazolopyridyl, thiazolopyrimidinyl, thiazolinopyridyl, thiazolinopyrimidinyl, oxothiazolinopyridyl, oxothiazolinopyrimidinyl, isothiazolopyridyl, isothiazolopyrimidinyl, imidazolopyridyl, imidazolinopyridyl, oxoimidazolinopyridyl, purinyl, imidazolinopyrimidinyl, oxoimidazolinopyrimidinyl, pyrazolopyridyl, pyrazolopyrimidinyl, pyrazolinopyridyl, pyrazolinopyrimidinyl, oxopyrazolinopyridyl, oxopyrazolinopyrimidinyl, naphthyridinyl, pyridopyrimidinyl, pyrimidopyrimidinyl and pteridinyl.

The term "heterocyclyl" refers to, unless otherwise further specified, a mono- or bicyclic-3–14 membered ring, that is totally saturated, with up to five ring heteroatoms selected from nitrogen, oxygen and sulphur wherein a —$CH_2$— group can optionally be replaced by a —C(O)— or a ring nitrogen atom may optionally bear a $C_{1-6}$alkyl group. Examples of such heterocyclyls include morpholinyl, N-methylmorpholinyl, pyrrolidinyl, imidazolidinyl, pyrazolidinyl, piperidinyl, N-methylpiperidinyl, piperazinyl and quinuclidinyl. When an $R^4$ group involves a $D^1$ group and $D^1$ is heterocyclyl, that "heterocyclyl" preferably refers to oxiranyl, oxetanyl, azetidinyl, tetrahydrofuranyl, tetrahydropyranyl, pyrrolidinyl, imidazolidinyl, pyrazolidinyl, 1,1-dioxidoisothiazolidinyl, morpholinyl, tetrahydro-1,4-thiazinyl, 1,1-dioxotetrahydro-1,4-thiazinyl, piperidinyl, homopiperidinyl, piperazinyl or homopiperazinyl, preferably to azetidin-1-yl, pyrrolidin-1-yl, pyrrolidin-2-yl, 1,1-dioxidoisothiazolidin-2-yl, morpholino, 1,1-dioxotetrahydro-4H-1,4-thiazin-4-yl, piperidin-3-yl, piperidin-4-yl, homopiperidin-1-yl, piperidino, piperazin-1-yl or homopiperazin-1-yl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

Where optional substituents are chosen from "one or more" groups it is to be understood that this definition includes all substituents being chosen from one of the specified groups or the substituents being chosen from two or more of the specified groups. Conveniently there may be 1, 2 or 3 such optional substituents. For example, where optional substituents are chosen from one or more groups selected from halo, $C_{1-6}$alkoxy and $C_{1-6}$alkyl, examples of possible combinations of substituents include 1) a bromo group, 2) two chloro groups, 3) a methoxy, ethoxy and propoxy substituent, 4) a fluoro and a methoxy group, 5) a methoxy, a methyl and an ethyl group, and 6) a chloro, a methoxy and an ethyl group.

Examples of $C_{1-4}$alkyl include methyl, ethyl and isopropyl. Examples of $C_{1-6}$alkoxycarbonyl include methoxycarbonyl, ethoxycarbonyl, n- and t-butoxycarbonyl. Examples of $C_{1-6}$alkoxy include $C_{1-4}$alkoxy and $C_{2-4}$alkoxy and include methoxy, ethoxy, propoxy and t-butoxy. Examples of $C_{1-6}$alkanoylamino include formamido, acetamido and propionylamino. Examples of $C_{1-6}$alkylS$(O)_n$ where n is 0–2 include methylthio, ethyltlhio, methylsulphinyl, ethylsulphinyl, methylsulphonyl and ethylsulphonyl. Examples of $C_{2-6}$alkanoyl include propionyl and acetyl. Examples of N-$C_{1-6}$alkylamino include N-methylamino and N-ethylamino. Examples of N,N-$(C_{1-6}$ alkyl$)_2$amino include N,N-dimethylamino, N,N-diethylamino and N-ethyl-N-methylamino. Examples of $C_{1-6}$alkoxy$C_{2-6}$alkoxy include methoxyethoxy and propoxybutoxy. Examples of N-($C_{1-6}$alkyl)amino$C_{2-6}$alkoxy include 3-(N-methylamino)propoxy and 4-(N-ethylamino)butoxy. Examples of N,N-$(C_{1-6}$alkyl$)_2$amino$C_{2-6}$alkoxy include 2-(N,N-dimethylamino)ethoxy and 3-(N-methyl-N-ethylamino)propoxy. Examples of $C_{3-7}$cycloalkyl include cyclopropyl and cyclohexyl. Examples of $C_{2-6}$alkenyl include vinyl, allyl and 1-propenyl. Examples of $C_{2-6}$alkynyl include ethynyl, 1-propynyl and 2-propynyl. Examples of hydroxy$C_{2-6}$alkoxy include 2-hydroxyethoxy and 2-hydroxyprcopoxy. Examples of $C_{1-6}$allkylsulphonylamino include methanesulphonamido and ethanesulphonamido. Examples of $C_{1-6}$alkylsulphonyl-N-($C_{1-6}$alkyl)amino include N-ethylmethanesulphonamido and N-butylethanesulphonamido. Examples of N-($C_{1-6}$alkyl) sulphamoyl include N-methylsulphamoyl and N-ethylsulphamoyl. Examples of N,N-$(C_{1-6}$alkyl$)_2$sulphamoyl include N,N-dimethylsulphamoyl and N-methyl-N-ethylsulphamoyl. Examples of N-($C_{1-6}$alkyl) carbamoyl include N-methylcarbamoyl and N-ethylcarbamoyl. Examples of N,N-$(C_{1-6}$alkyl$)_2$carbamoyl include N,N-dimethylcarbamoyl and N-methyl-N-ethylcarbamoyl. Examples of $C_{1-6}$alkanoyloxy include propionyloxy, acetyloxy and formyloxy. Examples of —O—$C_{1-3}$alkyl-O— include -oxyethoxy- and -oxymethoxy- (i.e. a bidentate substituent, attached to the ring in two adjacent positions).

In the linking groups B, E, $B^1$, $E^1$ and K that fall within the definition of $R^1$ and $R^4$, examples of generic terms include the following. Examples of $C_{1-6}$alkylene include —$CH_2CH_2$— and —$CH_2CH(CH_3)CH_2O$—. Examples of $C_{1-6}$alkyleneoxy include —$CH_2CH_2O$— and —$CH_2CH(CH_3)CH_2O$—. Examples of N-($C_{1-6}$alkyl)imino include —N(Me)- and —N($^i$Pr)-. Examples of $C_{1-6}$alkyleneimino include —$CH_2CH_2NH$— and —$CH_2CH(CH_3)CH_2NH$—. Examples of N-($C_{1-6}$alkyl)-$C_{1-6}$alkyleneimino include —$CH_2CH_2N$(Me)- and -$CH_2CH(CH_3)CH_2N$($^i$Pr)-. Examples of $C_{1-6}$alkanoylimino include —$CH_2CH_2C$(O)NH— and —$CH_2CH(CH_3)CH_2C$(O)NH—. Examples of oxy$C_{1-6}$alkylene include —$OCH_2CH_2$— and —$OCH_2CH(CH_3)CH_2$—. Examples of imino$C_{1-6}$alkylene include —$NHCH_2CH_2$— and —$NHCH_2CH(CH_3)CH_2$—. Examples of N-($C_{1-6}$alkyl)imino$C_{1-6}$alkylene include —N(Me)$CH_2CH_2$— and —N($^i$Pr)$CH_2CH(CH_3)CH_2$—. Examples of —NHC(O)$C_{1-6}$alkylene- include —NHC(O)$CH_2CH_2$— and —NHC(O)$CH_2CH(CH_3)CH_2$—.

When, as defined hereinbefore, any of the $R^1$ or $R^4$ groups defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, $C_{1-6}$alkoxy, N-$C_{1-6}$alkylamino, N,N-$(C_{1-6}$alkyl$)_2$amino and heterocyclyl, suitable substituents so formed include, for example, substituted heterocyclyl$C_{1-6}$alkoxy groups such as 2-hydroxy-3-piperidinopropoxy and 2-hydroxy-3-morpholinopropoxy, substituted amino$C_{1-6}$alkoxy groups such as 3-amino-2-hydroxypropoxy, substituted N-$C_{1-6}$alkylamino$C_{1-6}$alkoxy groups such as 2-hydroxy-3-methylaminopropoxy, substituted N,N)-$(C_{1-6}$alkyl$)_2$amino$C_{1-6}$alkoxy groups such as 3-dimethylamino-2-hydroxypropoxy, 3-[N-(3-dimethylaminopropyl)-N-methylamino]propoxy and 3-[N-(3-dimethylaminopropyl)-N-methylamino]-2-hydroxypropoxy, substituted heterocyclyl$C_{1-6}$alkylamino groups such as 2-hydroxy-3-piperidinopropylamino and 2-hydroxy-3-morpholinopropylamino, substituted amino$C_{1-6}$alkylamino groups such as 3-amino-2-hydroxypropylamino, substituted N-$C_{1-6}$alkylamino$C_{1-6}$alkylamino groups such as 2-hydroxy-3-methylaminopropylamino, substituted N,N-$(C_{1-6}$alkyl$)_2$amino$C_{1-6}$alkylamino groups such as 3-dimethylamino-2-hydroxypropylamino, 3-[N-(3-dimethylaminopropyl)-N-methylamino]propylamino and 3-[N-(3-dimethylaminopropyl)-N-methylamino]-2-hydroxypropylamino, substituted N-$C_{1-6}$alkylamino$C_{1-6}$alkyl groups such as 2-dimethylaminoethylaminomethyl, 3-dimethylaminopropylaminomethyl, 3-dimethylamino-2,2-dimethylpropylaminomethyl, 2-morpholinoethylaminomethyl, 2-piperazin-1-ylethylaminomethyl and 3-morpholinopropylaminomethyl.

Preferable values of $R^1$, $R^2$, $R^3$, $R^4$, $R^5$, G, X, q and m are as follows.

Preferably G is N or C(CN), more preferably G is N.

A preferred example of the diradical of a suitable fused heteroaryl ring for ring X is thiendiyl, furandiyl, imidazolediyl, pyrazolediyl, oxazolediyl, thiazolediyl, pyridinediyl, pyrimidinediyl or pyrazinediyl.

A more preferred example of the diradical of a suitable fused heteroaryl ring for ring X is thiendiyl, thiazolediyl, pyridinediyl or pyrazinediyl.

A preferred example of the mono-radical of a suitable bicyclic ring formed by the fusion of ring X to the adjacent nitrogen-containing 6-membered heteroaryl ring within Formula (I) is furopyrimidinyl, thienopyrimidinyl, pyrrolopyrimidinyl, pyrrolinopyrimidinyl, oxopyrrolinopyrimidinyl, oxazolopyrimidinyl, oxazolinopyrimidinyl, oxooxazolinopyrimidinyl, isoxazolopyrimidinyl, thiazolopyrimidinyl, thiazolinopyrimidinyl, oxothiazolinopyrimidinyl, isothiazolopyrimidinyl, purinyl, imidazolinopyrimidinyl, oxoimnidazolinopyrimidinyl, pyrazolopyrimidinyl, pyrazolinopyrimidinyl, oxopyrazolinopyrimidinyl, pyridopyrimidinyl, pyrimidopyrimidinyl or pteridinyl.

A more preferred example of the mono-radical of a suitable bicyclic ring formed by the fusion of ring X to the adjacent nitrogen-containing 6-membered heteroaryl ring within Formula (I) is furopyrimidinyl, thienopyrimidinyl, pyrrolopyrimidinyl, oxazolopyrimidinyl, thiazolopyrimidinyl, purinyl, pyridopyrimidinyl, pyrimidopyrimidinyl or pteridinyl.

A further more preferred example of the mono-radical of a suitable bicyclic ring formed by the fusion of ring X to the adjacent nitrogen-containing 6-membered heteroaryl ring within Formula (I) is furo[3,2-d]pyrimidinyl, furo[2,3-d]pyrimidinyl, thieno[3,2-d]pyrimidinyl, thieno[2,3-d]pyrimidinyl, pyrrolo[3,2-d]pyrimidinyl, pyrrolo[2,3-d]pyrimidinyl, oxazolo[5,4-d]pyrimidinyl, oxazolo[4,5-d]pyrimidinyl, thiazolo[5,4-d]pyrimidinyl, thiazolo[4,5-d]pyrimidinyl, purinyl, pyrido[2,3-d]pyrimidinyl, pyrido[3,4-d]pyrimidinyl, pyrido[4,3-d]pyrimidinyl, pyrido[3,2-d]pyrimidinyl, pyrimido[4,5-d]pyrimidinyl, pyrimido[5,6-d]pyrimidinyl or pteridinyl.

A particular preferred example of the mono-radical of a suitable bicyclic ring formed by the fusion of ring X to the adjacent nitrogen-containing 6-membered heteroaryl ring within Formula (I) is 6-oxopyrrolino[2,3-d]pyrimidin-4-yl, 6-oxopyrrolino[3,2-d]pyrimidin-4-yl, 2-oxooxazolino[5,4-d]pyrimidin-7-yl, 2-oxothiazolino[5,4-d]pyrimidin-7-yl, 2-oxooxazolino[4,5-d]pyrimidin-7-yl, 2-oxothiazolino[4,5-d]pyrimidin-7-yl, 2-oxoimidazolino[4,5-d]pyrimidin-7-yl, 3-oxopyrazolino[3,4-d]pyrimidin-4-yl or 3-oxopyrazolino[4,3-d]pyrimidin-7-yl.

A further more preferred example of the mono-radical of a suitable bicyclic ring formed by the fusion of ring X to the adjacent nitrogen-containing 6-membered heteroaryl ring within Formula (I) is thieno[3,2-d]pyrimidinyl, thieno[2,3-d]pyrimidinyl, thiazolo[5,4-d]pyrimidinyl, pyrido[2,3-d]pyrimidinyl, pyrido[3,4-d]pyrimidinyl, pyrido[4,3-d]pyrimidinyl, pyrido[3,2-d]pyrimidinyl or pteridinyl.

Particularly, a more preferred example of the mono-radical of a suitable bicyclic ring formed by the fusion of ring X to the adjacent nitrogen-containing 6-membered heteroaryl ring within Formula (I) is thieno[3,2-d]pyrimidin-4-yl, thieno[2,3-d]pyrimidin-4-yl, thiazolo[5,4-d]pyrimidin-7-yl, pyrido[2,3-d]pyrimidin-4-yl, pyrido[3,4-d]pyrimidin-4-yl, pyrido[4,3-d]pyrimidin-4-yl, pyrido[3,2-d]pyrimidin-4-yl or pteridin-4-yl.

Preferably m is 0 or m is 1 or 2 and each $R^1$ is independently hydroxy, halo, $C_{1-6}$alkyl, $C_{1-6}$alkoxy, $C_{1-6}$alkylS(O)$_n$— (wherein n is 0–2), N,N-($C_{1-6}$alkyl)$_2$amino$C_{1-6}$alkyl, N,N-($C_{1-6}$alkyl)$_2$carbamoyl$C_{1-6}$alkoxy, N,N-($C_{1-6}$alkyl)$_2$amino$C_{1-6}$alkoxy, $C_{1-6}$alkylS(O)$_2$—$C_{1-6}$alkoxy, N,N-($C_{1-6}$ alkyl)$_2$amino-N-($C_{1-6}$alkyl)$C_{1-6}$alkylamino, N,N-($C_{1-6}$ alkyl)$_2$amino$C_{1-6}$alkylamino$C_{1-6}$alkyl, heterocyclyl$C_{1-6}$ alkyl, heterocyclyl$C_{1-6}$alkoxy, heterocyclyloxy, heterocyclyl$C_{1-6}$alkylamino$C_{1-6}$alkyl or heteroaryl$C_{1-6}$ alkoxy.

More preferably m is 0 or m is 1 and each $R^1$ is independently hydroxy, halo, $C_{1-6}$alkyl, $C_{1-6}$alkoxy, $C_{1-6}$alkylS(O)$_n$— (wherein n is 0–2), N,N-($C_{1-6}$alkyl)$_2$amino$C_{1-6}$alkyl, N,N-($C_{1-6}$alkyl)$_2$carbamoyl$C_{1-6}$alkoxy, N,N-($C_{1-6}$alkyl)$_2$amino$C_{1-6}$alkoxy, $C_{1-6}$alkylS(O)$_2$—$C_{1-6}$ alkoxy, N,N-($C_{1-6}$alkyl)$_2$amino-N-($C_{1-6}$alkyl)$C_{1-6}$ alkylamino, N,N-($C_{1-6}$alkyl)$_2$amino$C_{1-6}$alkylamino$C_{1-6}$ alkyl, piperidin-1-yl$C_{1-6}$alkyl, homopiperidin-1-yl$C_{1-6}$ alkyl, N-($C_{1-6}$alkyl)piperidin-1-yl$C_{1-6}$alkyl, N-($C_{1-6}$alkyl)homopiperidin-1-yl$C_{1-6}$alkyl, piperazin-1-yl$C_{1-6}$alkyl, 4-$C_{1-6}$ alkylpiperazin-1-yl$C_{1-6}$alkyl, homopiperazinyl-1-yl$C_{1-6}$ alkyl, 4-$C_{1-6}$alkylhomopiperazinyl-1-yl$C_{1-6}$alkyl, pyrrolidinyl$C_{1-6}$alkoxy, piperidinyl$C_{1-6}$alkoxy, homopiperidinyl$C_{1-6}$alkoxy, N-($C_{1-6}$alkyl)pyrrolidinyl$C_{1-6}$ alkoxy, N-($C_{1-6}$alkyl)piperidinyl$C_{1-6}$alkoxy, N-($C_{1-6}$alkyl)homopiperidinyl$C_{1-6}$alkoxy, morpholinyl$C_{1-6}$alkoxy, piperazinyl$C_{1-6}$alkoxy, N-($C_{1-6}$alkyl)piperazinyl$C_{1-6}$alkoxy, homopiperazinyl$C_{1-6}$alkoxy, N-($C_{1-6}$alkyl)homopiperazinyl$C_{1-6}$alkoxy, pyrrolidinyloxy, N-($C_{1-6}$alkyl)pyrrolidinyloxy, piperidinyloxy, N-($C_{1-6}$alkyl)piperidinyloxy, homopiperidinyloxy, N-($C_{1-6}$alkyl)homopiperidinyloxy, morpholinyl$C_{1-6}$alkylamino$C_{1-6}$alkyl, thiazolyl$C_{1-6}$alkoxy or pyridyl$C_{1-6}$alkoxy.

Further more preferably m is 0 or m is 1 and each $R^1$ is independently hydroxy, halo, $C_{1-6}$alkyl, $C_{1-6}$alkoxy, $C_{1-6}$alkylS(O)$_n$— (wherein n is 0–2), N,N-($C_{1-6}$alkyl)$_2$amino$C_{1-6}$alkyl, N,N-($C_{1-6}$alkyl)$_2$carbamoyl$C_{1-6}$alkoxy, N,N-($C_{1-6}$alkyl)$_2$amino$C_{1-6}$alkoxy, $C_{1-6}$alkylS(O)$_2$—$C_{1-6}$ alkoxy, N,N-$C_{1-6}$alkyl)$_2$amino-N-($C_{1-6}$alkyl)$C_{1-6}$ alkylamino, N,N-($C_{1-6}$alkyl)$_2$amino$C_{1-6}$alkylamino$C_{1-6}$ alkyl, piperazin-1-yl$C_{1-6}$alkyl, 4-$C_{1-6}$alkylpiperazin-1-yl$C_{1-6}$ alkyl, homopiperazinyl-1-yl$C_{1-6}$alkyl, 4-$C_{1-6}$ alkylhomopiperazinyl-1-yl$C_{1-6}$alkyl, pyrrolidinyl$C_{1-6}$ alkoxy, piperidinyl$C_{1-6}$alkoxy, N-($C_{1-6}$alkyl)pyrrolidinyl$C_{1-6}$alkoxy, N-($C_{1-6}$alkyl)piperidinyl$C_{1-6}$ alkoxy, morpholinyl$C_{1-6}$alkoxy, piperazinyl$C_{1-6}$alkoxy, N-($C_{1-6}$alkyl)piperazinyl$C_{1-6}$alkoxy, homopiperazinyl$C_{1-6}$ alkoxy, N-($C_{1-6}$alkyl)homopiperazinyl$C_{1-6}$alkoxy, pyrrolidinyloxy, piperidinyloxy, morpholinyl$C_{1-6}$ alkylamino$C_{1-6}$alkyl or pyridyl$C_{1-6}$alkoxy.

More particularly m is 0 or m is 1 and each $R^1$ is independently methyl, methoxy, methylthio, methylsulphinyl, methylsulphonyl, 2-dimethylaminoethoxy, 2-diethylaminoethoxy, 2-diisopropylamninoethoxy, 3-dimethylaminopropoxy, 3-diethylaminopropoxy, 2-morpholinoethoxy, 3-morpholinopropoxy, 2-piperidinoethoxy, N-methylpiperidin-2-ylmethoxy, N-methylpiperidin-3-ylmethoxy, 2-pyrrolidin-1-ylethoxy, 2-(N-methylpyrrolidin-2-yl)ethoxy, N-methyl-5-oxopyrrolidin-2-ylmethoxy, 3-pyrrolidin-1-ylpropoxy, 2-(2-oxoimidazolidin-1-yl)ethoxy, 2-(4-methylpiperazin-1-yl)ethoxy or 3-pyrid-3-ylpropoxy.

Further more particularly m is 0 or m is 1 and each $R^1$ is independently methyl, ethoxy, methylthio, 2-diisopropylaminoethoxy, 3-diethylaminopropoxy, 3-morpholinopropoxy or 3-pyrrolidin-1-ylpropoxy.

Even more particularly m is 0 or m is 1 and $R^1$ is methyl or methylthio.

Preferably $R^2$ is hydrogen, $C_{1-6}$alkyl or halo.

More preferably $R^2$ is hydrogen, $C_{1-4}$alkyl or halo.

Particularly $R^2$ is hydrogen, methyl, fluoro or chloro, more particularly methyl.

Preferably $R^3$ is hydrogen, $C_{1-6}$alkyl or halo.

More preferably $R^3$ is hydrogen, $C_{1-4}$alkyl or halo.

Particularly $R^3$ is hydrogen, methyl, fluoro or chloro, more particularly hydrogen.

Preferably q is 0 or 1, more preferably q is 0.

Preferably $R^4$ is aryl or heteroaryl optionally substituted by one or more groups elected from halo, cyano, $C_{1-6}$alkyl, $C_{1-6}$alkoxy, N,N-($C_{1-6}$alkyl)$_2$amino or heterocyclyl.

More preferably $R^4$ is aryl or heteroaryl optionally substituted by one or more groups elected from halo, cyano, $C_{1-6}$alkyl, $C_{1-6}$alkoxy, N,N-($C_{1-6}$alkyl)$_2$amino, pyrrolidin-1-yl, piperidinyl, morpholino, piperazinyl, 4-$C_{1-6}$ alkylpiperazin-1-yl, homopiperazinyl-1-yl or 4-$C_{1-6}$ alkylhomopiperazinyl-1-yl.

Further more preferably $R^4$ is phenyl, thienyl, furyl, oxazolyl, isoxazolyl, pyrimidyl or pyridyl optionally substituted by one or two halo, trifluoromethyl, cyano, $C_{1-4}$alkyl, $C_{1-4}$alkoxy, —O—($C_{1-3}$alkyl)-O—, N,N-($C_{1-4}$alkyl)$_2$amino, $C_{1-6}$alkanoylamino, $C_{1-6}$alkylsulphonyl-N-($C_{1-6}$alkyl) amino, phenyl (optionally substituted by one or two halo groups), furyl, azetidinyl, pyrrolidinyl, 3-pyrrolinyl, piperidino, homopiperidinyl, morpholino, piperazinyl, homopiperazinyl, N-($C_{1-6}$alkyl)piperazinyl and N-($C_{1-6}$alkyl)homopiperazinyl, or $R^4$ is fluorenyl or dibenzofuranyl.

Further more preferably $R^4$ is phenyl, thienyl, furyl, oxazolyl, isoxazolyl, pyrimidyl or pyridyl optionally substituted by one or two halo, cyano, $C_{1-4}$alkyl, $C_{1-4}$alkoxy, N,N-($C_{1-4}$alkyl)$_2$amino, piperidinyl, morpholino or piperazinyl.

Particularly $R^4$ is phenyl, furyl, isoxazolyl or pyridyl optionally substituted by one or more groups selected from fluoro, chloro, cyano, methyl, methoxy, N,N-dimethylamino or morpholino.

Further particularly $R^4$ is phenyl, furyl, thienyl or pyridyl optionally substituted by one or two groups selected from fluoro, chloro, trifluoromethyl, cyano, methyl, methoxy, ethoxy, methylenedioxy, N,N-dimethylamino, acetamido, N-methylmethanesulphonamido, phenyl, 4-fluorophenyl, 4-chlorophenyl, furyl, azetidin-1-yl, pyrrolidin-1-yl, 3-pyrrolin-1-yl, piperidino, homopiperidin-1-yl, morpholino, piperazin-1-yl, homopiperazin-1-yl, 4-methylpiperazin-1-yl and 4-methylhomopiperazin-1-yl.

Further particularly $R^4$ is phenyl optionally substituted by one or two groups selected from fluoro, chloro, trifluoromethyl, cyano, methyl, methoxy, ethoxy, methylenedioxy, N,N-dimethylamino, acetamido, N-methylmethanesulphonamido, phenyl, 4-fluorophenyl, 4-chlorophenyl, 2-furyl, azetidin-1-yl, pyrrolidin-1-yl, 3-pyrrolin-1-yl, piperidino, homopiperidin-1-yl, morpholino, piperazin-1-yl, homopiperazin-1-yl, 4-methylpiperazin-1-yl and 4-methylhomopiperazin-1-yl.

Further particularly $R^4$ is 1-fluorenyl or dibenzofuran-4-yl.

More particularly $R^4$ is phenyl, 2-methylphenyl, 3-(N,N-dimethylamino)phenyl, 3-fluorophenyl, 3-methoxyphenyl, 4-cyanophenyl, 3,4-dimethoxyphenyl, 3-morpholinophenyl, 2-furyl, 2-chloropyrid-5-yl, 2-morpholinopyrid-4-yl or isoxazol-5-yl.

Further more particularly $R^4$ is phenyl, 3-fluorophenyl, 4-cyanophenyl, 2-methylphenyl, 2-methoxyphenyl, 3-methoxyphenyl, 3-ethoxyphenyl, 3,4-dimethoxyphenyl, 3,4-methylenedioxyphenyl, 3-(N,N-dimethylamino)phenyl, 3-acetamidophenyl, 3-(4-fluorophenyl)phenyl, 3-(2-furyl) phenyl, 3-pyrrolidin-1-ylphenyl, 3-morpholinophenyl, 3-fluoro-5-pyrrolidin-1-ylphenyl, 3-fluoro-5-piperidinophenyl, 3-fluoro-5-morpholinophenyl or 3-morpholino-5-trifluoromethylphenyl.

Further more particularly $R^4$ is pyridyl optionally substituted by a N,N-dimethylamino, N,N-diethylamino, pyrrolidin-1-yl, piperidino or morpholino group.

Further more particularly $R^4$ is pyridyl optionally substituted by a N,N-dimethylamino, N,N-diethylamino, azetidin-1-yl, pyrrolidin-1-yl, 3-pyrrolin-1-yl, piperidino, homopiperidin-1-yl, morpholino, piperazin-1-yl, homopiperazin-1-yl, 4-methylpiperazin-1-yl or 4-methylhomopiperazin-1-yl group.

Even more particularly $R^4$ is 2-morpholinopyrid-4-yl.

Preferably $R^4$ is hydrogen or $C_{1-6}$alkoxy, more preferably $C_{1-4}$alkoxy, particularly hydrogen or methoxy.

Preferably $R^5$ is hydrogen.

According to a preferred aspect of the invention, there is provided a compound of the Formula (I) wherein:

the bicyclic ring formed by the fusion of ring X to the adjacent nitrogen-containing 6-membered heteroaryl ring within Formula (I) is furopyrimidinyl, thienopyrimidinyl, pyrrolopyrimidinyl, oxazolopyrimidinyl, thiazolopyrimidinyl, purinyl, pyridopyrimidinyl, pyrimidopyrimidinyl or pteridinyl;

m is 0 or m is 1 and each $R^1$ is independently hydroxy, halo, $C_{1-6}$alkyl, $C_{1-6}$alkoxy, $C_{1-6}$alkylS(O)$_n$— (wherein n is 0–2), N,N-($C_{1-6}$alkyl)$_2$amino$C_{1-6}$alkyl, N,N-($C_{1-6}$ alkyl)$_2$carbamoyl$C_{1-6}$alkoxy, N,N-($C_{1-6}$alkyl)$_2$ amino$C_{1-6}$alkoxy, $C_{1-6}$alkylS(O)$_2$—$C_{1-6}$alkoxy, N,N-($C_{1-6}$alkyl)$_2$amino-N-($C_{1-6}$alkyl)$C_{1-6}$alkylamino, N,N-($C_{1-6}$alkyl)$_2$amino$C_{1-6}$alkylamino$C_{1-6}$alkyl, piperidin-1-yl$C_{1-6}$alkyl, homopiperidin-1-yl$C_{1-6}$alkyl, N-($C_{1-6}$ alkyl)piperidin-1-yl$C_{1-6}$alkyl, N-($C_{1-6}$alkyl) homopiperidin-1-yl$C_{1-6}$alkyl, piperazin-1-yl$C_{1-6}$alkyl, 4-$C_{1-6}$alkylpiperazin-1-yl$C_{1-6}$alkyl, homopiperazinyl-1-yl$C_{1-6}$alkyl, 4-$C_{1-6}$alkylhomopiperazinyl-1-yl$C_{1-6}$ alkyl, pyrrolidinyl$C_{1-6}$alkoxy, piperidinyl$C_{1-6}$alkoxy, homopiperidinyl$C_{1-6}$alkoxy, N-($C_{1-6}$alkyl) pyrrolidinyl$C_{1-6}$alkoxy, N-($C_{1-6}$alkyl)piperidinyl$C_{1-6}$ alkoxy, N-($C_{1-6}$alkyl)homopiperidinyl$C_{1-6}$alkoxy, morpholinyl$C_{1-6}$alkoxy, piperazinyl$C_{1-6}$alkoxy, N-($C_{1-6}$ alkyl)piperazinyl$C_{1-6}$alkoxy, homopiperazinyl$C_{1-6}$alkoxy, N-($C_{1-6}$alkyl) homopiperazinyl$C_{1-6}$alkoxy, pyrrolidinyloxy, N-($C_{1-6}$alkyl)pyrrolidinyloxy, piperidinyloxy, N-($C_{1-6}$alkyl) piperidinyloxy, homopiperidinyloxy, N-($C_{1-6}$alkyl) homopiperidinyloxy, morpholinyl$C_{1-6}$alkylamino$C_{1-6}$alkyl, thiazolyl$C_{1-6}$alkoxy or pyridyl$C_{1-6}$alkoxy;

$R^2$ is hydrogen, $C_{1-4}$alkyl or halo;

$R^3$ is hydrogen, $C_{1-4}$alkyl or halo;

q is 0;

$R^4$ is phenyl, thienyl, furyl, oxazolyl, isoxazolyl, pyrimidyl or pyridyl optionally substituted by one or two halo, trifluoromethyl, cyano, $C_{1-4}$alkyl, $C_{1-4}$alkoxy, —O—($C_{1-3}$alkyl)—O—, N,N-($C_{1-4}$alkyl)$_2$amino, $C_{1-6}$alkanoylamino, $C_{1-6}$alkylsulphonyl-N-($C_{1-6}$alkyl) amino, phenyl (optionally substituted by one or two halo groups), furyl, azetidinyl, pyrrolidinyl, 3-pyrrolinyl, piperidino, homopiperidinyl, morpholino, piperazinyl, homopiperazinyl, N-($C_{1-6}$alkyl)

piperazinyl and N-($C_{1-6}$alkyl)homopiperazinyl, or $R^4$ is fluorenyl or dibenzofuranyl; and $R^5$ is hydrogen;

or a pharmaceutically acceptable salt or an in vivo cleavable ester thereof

According to a further preferred aspect of the invention, there is provided a compound of the Formula (I) wherein:

the bicyclic ring formed by the fusion of ring X to the adjacent nitrogen-containing 6-membered heteroaryl ring within Formula (I) is furopyrimidinyl, thienopyrimidinyl, pyrrolopyrimidinyl, oxazolopyrimidinyl, thiazolopyrimidinyl, purinyl, pyridopyrimidinyl, pyrimidopyrimidinyl or pteridinyl;

m is 0 or m is 1 and each $R^1$ is independently hydroxy, halo, $C_{1-6}$alkyl, $C_{1-6}$alkoxy, $C_{1-6}$alkylS(O)$_n$— (wherein n is 0–2), N,N-($C_{1-6}$alkyl)$_2$amino$C_{1-6}$alkyl, N,N-($C_{1-6}$alkyl)$_2$carbamoyl$C_{1-6}$alkoxy, N,N-($C_{1-6}$alkyl)$_2$amino$C_{1-6}$alkoxy, $C_{1-6}$alkylS(O)$_2$—$C_{1-6}$alkoxy, N,N-($C_{1-6}$alkyl)$_2$amino-N-($C_{1-6}$alkyl)$C_{1-6}$alkylamino, N,N-($C_{1-6}$alkyl)$_2$amino$C_{1-6}$alkylamino$C_{1-6}$alkyl, piperazin-1-yl$C_{1-6}$alkyl 4-$C_{1-6}$alkylpiperazin-1-yl$C_{1-6}$alkyl, homopiperazinyl-1-yl$C_{1-6}$alkyl, 4-$C_{1-6}$alkylhomopiperazinyl-1-yl$C_{1-6}$alkyl, pyrrolidinyl$C_{1-6}$alkoxy, piperidinyl$C_{1-6}$alkoxy, N-($C_{1-6}$alkyl)pyrrolidinyl$C_{1-6}$alkoxy, N-($C_{1-6}$alkyl)piperidinyl$C_{1-6}$alkoxy, morpholinyl$C_{1-6}$alkoxy, piperazinyl$C_{1-6}$alkoxy, N-($C_{1-6}$alkyl)piperazinyl$C_{1-6}$alkoxy, homopiperazinyl$C_{1-6}$alkoxy, N-($C_{1-6}$alkyl)homopiperazinyl$C_{1-6}$alkoxy, pyrrolidinyloxy, piperidinyloxy, morpholinyl$C_{1-6}$alkylamino$C_{1-6}$alkyl or pyridyl$C_{1-6}$alkoxy;

$R^2$ is hydrogen, $C_{1-4}$alkyl or halo;

$R^3$ is hydrogen, $C_{1-4}$alkyl or halo;

q is 0;

$R^4$ is phenyl, thienyl, furyl, oxazolyl, isoxazolyl, pyrimidyl or pyridyl optionally substituted by one or two halo, cyano, $C_{1-4}$alkyl, $C_{1-4}$alkoxy, N,N-($C_{1-4}$alkyl)$_2$amino, piperidinyl, morpholino or piperazinyl; and $R^5$ is hydrogen;

or a pharmaceutically acceptable salt or an in vivo cleavable ester thereof.

In a more preferred aspect of the invention there is provided a compound of the Formula (I) wherein:

the bicyclic ring formed by the fusion of ring X to the adjacent nitrogen-containing 6-membered heteroaryl ring within Formula (I) is furo[3,2-d]pyrimidinyl, furo[2,3-d]pyrimidinyl, thieno[3,2-d]pyrimidinyl, thieno[2,3-d]pyrimidinyl, pyrrolo[3,2-d]pyrimidinyl, pyrrolo[2,3-d]pyrimidinyl, oxazolo[5,4-d]pyrimidinyl, oxazolo[4,5-d]pyrimidinyl, thiazolo[5,4-d]pyrimidinyl, thiazolo[4,5-d]pyrimidinyl, purinyl, pyrido[2,3-d]pyrimidinyl, pyrido[3,4-d]pyrimidinyl, pyrido[4,3-d]pyrimidinyl, pyrido[3,2-d]pyrimidinyl, pyrimido[4,5-d]pyrimidinyl, pyrimido[5,6-d]pyrimidinyl or pteridinyl;

m is 0 or m is 1 and each $R^1$ is independently methyl, methoxy, methylthio, 2-diisopropylaminoethoxy, 3-diethylaminopropoxy, 3-morpholinopropoxy or 3-pyrrolidin-1-ylpropoxy;

$R^2$ is hydrogen, methyl, fluoro or chloro;

$R^3$ is hydrogen;

q is 0;

$R^4$ is phenyl optionally substituted by one or two groups selected from fluoro, chloro, trifluoromethyl, cyano, methyl, methoxy, ethoxy, methylenedioxy, N,N-dimethylamino, acetamido, N-methylmethanesulphonamido, phenyl, 4-fluorophenyl, 4-chlorophenyl, 2-furyl, azetidin-1-yl, pyrrolidin-1-yl, 3-pyrrolin-1-yl, piperidino, homopiperidin-1-yl, morpholino, piperazin-1-yl, homopiperazin-1-yl, 4-methylpiperazin-1-yl and 4-methylhomopiperazin-1-yl, or $R^4$ is pyridyl optionally substituted by a N,N-dimethylamino, N,N-diethylamino, azetidin-1-yl, pyrrolidin-1-yl, 3-pyrrolin-1-yl, piperidino, homopiperidin-1-yl, morpholino, piperazin-1-yl, homopiperazin-1-yl, 4-methylpiperazin-1-yl or 4-methylhomopiperazin-1-yl group, or $R^4$ is 1-fluorenyl or dibenzofuran-4-yl; and $R^5$ is hydrogen;

or a pharmaceutically acceptable salt or an in vivo cleavable ester thereof.

In a further more preferred aspect of the invention there is provided a compound of the Formula (I) wherein:

the bicyclic ring formed by the fusion of ring X to the adjacent nitrogen-containing 6-membered heteroaryl ring within Formula (I) is furo[3,2-d]pyrimidinyl, furo[2,3-d]pyrimidinyl, thieno[3,2-d]pyrimidinyl, thieno[2,3-d]pyrimidinyl, pyrrolo[3,2-d]pyrimidinyl, pyrrolo[2,3-d]pyrimidinyl, oxazolo[5,4-d]pyrimidinyl, oxazolo[4,5-d]pyrimidinyl, thiazolo[5,4-d]pyrimidinyl, thiazolo[4,5-d]pyrimidinyl, purinyl, pyrido[2,3-d]pyrimidinyl, pyrido[3,4-d]pyrimidinyl, pyrido[4,3-d]pyrimidinyl, pyrido[3,2-d]pyrimidinyl, pyrimido[4,5-d]pyrimidinyl, pyrimido[5,6-d]pyrimidinyl or pteridinyl;

m is 0 or m is 1 and each $R^1$ is independently methyl, methoxy, methylthio, 2-diisopropylaminoethoxy, 3-diethylaminopropoxy, 3-morpholinopropoxy or 3-pyrrolidin-1-ylpropoxy;

$R^2$ is hydrogen, methyl, fluoro or chloro;

$R^3$ is hydrogen;

q is 0;

$R^4$ is pyridyl optionally substituted by a N,N-dimethylamino, N,N-diethylamino, pyrrolidin-1-yl, piperidino or morpholino group; and $R^5$ is hydrogen;

or a pharmaceutically acceptable salt or an in vivo cleavable ester thereof.

In a particular aspect of the invention there is provided a compound of the Formula (I) wherein:

the bicyclic ring formed by the fusion of ring X to the adjacent nitrogen-containing 6-membered heteroaryl ring within Formula (I) is thieno[3,2-d]pyrimidin-4-yl, thieno[2,3-d]pyrimidin-4-yl, thiazolo[5,4-d]pyrimidin-7-yl, 6-purinyl, pyrido[2,3-d]pyrimidin-4-yl, pyrido[3,4-d]pyrimidin-4-yl, pyrido[4,3-d]pyrimidin-4-yl, pyrido[3,2-d]pyrimidin-4-yl or pteridin-4-yl;

m is Q or m is 1 and $R^1$ is methyl or methylthio;

$R^2$ is methyl;

$R^3$ is hydrogen;

q is 0;

$R^4$ is phenyl, 3-fluorophenyl, 4-cyanophenyl, 2-methylphenyl, 2-methoxyphenyl, 3-methoxyphenyl, 3-ethoxyphenyl, 3,4-dimethoxyphenyl, 3,4-methylenedioxyphenyl, 3-(N,N-dimethylamino)phenyl, 3-acetamidophenyl, 3-(4-fluorophenyl)phenyl, 3-(2-furyl)phenyl, 3-pyrrolidin-1-ylphenyl, 3-morpholinophenyl, 3-fluoro-5-pyrrolidin-1-ylphenyl, 3-fluoro-5-piperidinophenyl, 3-fluoro-5-morpholinophenyl or 3-morpholino-5-trifluoromethylphenyl, or $R^4$ is 2-morpholinopyrid-4-yl, or $R^4$ is 1-fluorenyl or dibenzofuran-4-yl; and $R^5$ is hydrogen;

or a pharmaceutically acceptable salt or an in vivo cleavable ester thereof.

In a further particular aspect of the invention there is provided a compound of the Formula (I) wherein:

the bicyclic ring formed by the fusion of ring X to the adjacent nitrogen-containing 6-membered heteroaryl ring within Formula (1) is thieno[3,2-d]pyrimidin-4-yl, thieno[2,3-d]pyrimidin-4-yl, thiazolo(5,4-d]pyrimidin-7-yl, pyrido[2,3-d]pyrimidin-4-yl, pyrido[3,4-d] pyrimidin-4-yl, pyrido[4,3-d]pyrimidin-4-yl, pyrido[3, 2-d]pyrimidin-4-yl or pteridin-4-yl;

m is 0 or m is 1 and $R^1$ is methyl or methylthio;

$R^2$ is methyl;

$R^3$ is hydrogen;

q is 0;

$R^4$ is 2-morpholinopyrid-4-yl; and $R^5$ is hydrogen;

or a pharmaceutically acceptable salt or an in vivo cleavable ester thereof

Preferred compounds of the invention are those of Examples 1–3 or pharmaceutically acceptable salts or in vivo cleavable esters thereof.

An especially preferred compound of the invention is, for example, a compound of the Formula (I) selected from:

4-[2-methyl-5-(2-morpholinopyridine-4-carboxamido) anilino]thieno[3,2-d]pyrimidine, 4-[2-methyl-5-(2-morpholinopyridine-4-carboxamido) anilino]pyrido[4,3-d]pyrimidine, 4-[2-methyl-5-(2-morpholinopyridine-4-carboxamido) anilino]pteridine and 6-[2-methyl-5-(2-morpholinopyridine-4-carboxamido) anilino]purine;

or a pharmaceutically acceptable salt or an in vivo cleavable ester thereof.

A suitable pharmaceutically acceptable salt of a compound of the Formula (I) is, for example, an acid-addition salt of a compound of the Formula (I) which is sufficiently basic, for example an acid-addition salt with an inorganic or organic acid such as hydrochloric, hydrobromic, sulphuric, trifluoroacetic, citric or maleic acid; or, for example a salt of a compound of the Formula (I) which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

Examples of such pro-drugs may be used to form in vivo cleavable esters of a compound of the Formula (I). An ill vivo cleavable ester of a compound of the Formula (I) containing a carboxy group is, for example, a pharmaceutically acceptable ester which is cleaved in the human or animal body to produce the parent acid. Suitable pharmaceutically acceptable esters for carboxy include $C_{1-6}$alkoxymethyl esters, for example methoxymethyl; $C_{1-6}$alkanoyloxymethyl esters, for example pivaloyloxymethyl; phthalidyl esters; $C_{3-8}$cycloalkoxycarbonyloxy$C_{1-6}$alkyl esters, for example 1-cyclohexylcarbonyloxyethyl; 1,3-dioxolan-2-ylmethyl esters, for example 5-methyl-1,3-dioxolan-2-ylmethyl; and $C_{1-6}$alkoxycarbonyloxyethyl esters, for example 1-methoxycarbonyloxyethyl; and may be formed at any carboxy group in the compounds of this invention.

In order to use a compound of the Formula (I), or a pharmaceutically acceptable salt or in vivo cleavable ester thereof, for the therapeutic treatment (including prophylactic treatment) of mammals including humans, it is normally formulated in accordance with standard pharmaceutical practice as a pharmaceutical composition.

According to this aspect of the invention there is provided a pharmaceutical composition which comprises a bicyclic compound of the Formula (I), or a pharmaceutically acceptable salt or in vivo cleavable ester thereof, as defined hereinbefore in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parentally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insulation may be in the form of a finely divided powder containing particles of average diameter of, for example, 30 $\mu$m or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (I) will naturally vary according to the nature and severity of the conditions, the age and sex of the animal or patient and the route of administration, according to well known principles of medicine.

In using a compound of the Formula (I) for therapeutic or prophylactic purposes it will generally be administered so that a daily dose in the range, for example, 0.5 mg to 75 mg per, kg body weight, preferably 0.5 mg to 40 mg per kg body weight, is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about I mg to 500 mg of a compound of this invention.

The compounds of this invention may be used in combination with other drugs and therapies used in the treatment of disease states which would benefit from the inhibition of cytokines, in particular TNT and IL-1. For example, the compounds of the Formula (I) could be used in combination with drugs and therapies used in the treatment of rheumatoid arthritis, asthma, irritable bowel disease, multiple sclerosis, AIDS, septic shock, ischaemic heart disease, psoriasis and the other disease states mentioned earlier in this specification.

For example, by virtue of their ability to inhibit cytokines, the compounds of the Formula (I) are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicylic acid, ibuprofen, sulindac, tolmetin and piroxicam. Co-administration of a compound of the Formula (I) with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula (I), or a pharmaceutically acceptable salt or in vivo cleavable ester thereof, in conjunction or admixture with a cyclooxygenase inhibitory non-steroidal anti-inflammatory agent, and a pharmaceutically acceptable diluent or carrier.

The compounds of the invention may also be used with anti-inflammatory agents such as an inhibitor of the enzyme 5-lipoxygenase (such as those disclosed in European Patent Applications Nos. 0351194, 0375368, 0375404, 0375452. 0375457, 0381375, 0385662, 0385663, 0385679, 0385680).

The compounds of the Formula (I) may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, antidegradative and/or reparative agents such as Diacerhein, hyaluronic acid formulations such as Hyalan, Rumalon, Arteparon and glucosamine salts such as Antril.

The compounds of the Formula (I) may be used in the treatment of asthma in combination with antiasthmatic agents such as bronchodilators and leukotriene antagonists.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula (I) are primarily of value as therapeutic agents for use in warm-blooded animals (including man), they are also useful whenever it is required to inhibit the effects of cytokines. Thus, they are useful as pharmacological standards for use in the development of new biological tests and in the search for new pharmacological agents.

According to a further aspect of the present invention, there is provided a process for preparing a compound of the Formula (I), or a pharmaceutically acceptable salt or an in vivo cleavable ester thereof, which process (wherein G, $R^1$, $R^2$, $R^3$, $R^4$, $R^5$, ring X, m and q are as defined for Formula (I) unless otherwise stated) comprises of:

a) reacting an aniline of the Formula (II):

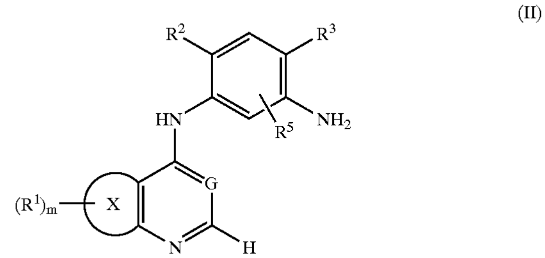

with an acyl compound of the Formula (III):

(III)

O

L (CH2)q R4 wherein L is a displaceable group as defined below;

b) reacting an activated bicyclic heteroaryl ring of the Formula (IV):

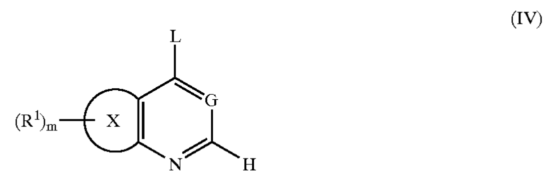

wherein L is a displaceable group as defined below, with an aniline of the Formula (V):

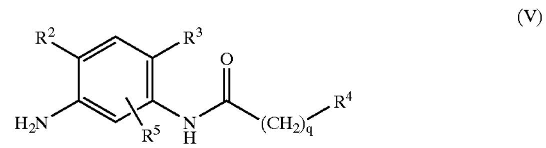

or c) for the preparation of a compound of the Formula (I) wherein $R^1$ or a substituent on $R^4$is $C_{1-6}$alkoxy or substituted $C_{1-6}$alkoxy, $C_{1-6}$alkylS—, N-$C_{1-6}$alkylamino, N,N-($C_{1-6}$alkyl)$_2$amino or substituted $C_{1-6}$alkylamino, the alkylation, conveniently in the presence of a suitable base as defined below, of a compound of the Formula (I) wherein $R^1$ or a substituent on $R^4$ is hydroxy, mercapto or amino as appropriate;

and thereafter if necessary:

i) converting a compound of the Formula (I) into another compound of the Formula (I);

ii) removing any protecting groups; and iii) forming a pharmaceutically acceptable salt or in vivo cleavable ester.

Specific reaction conditions for the above process variants are as follows:

For process variant a) A suitable displaceable group L is, for example, a halogeno, activated phenoxy group or sulphonyloxy group, for example a chloro, bromo, pentafluorophenoxy or methanesulphonyloxy or toluene-4-sulphonyloxy group. Especially preferred displaceable groups are chloro and pentafluorophenoxy.

Anilines of the Formula (II) and acyl compounds of the Formula (III) may be reacted together in a suitable inert solvent or diluent, for example dichloromethane, acetonitrile. butanol, tetramethylene sulphone, tetrahydrofuran, 1,2-dimethoxyethane, N,N-dimethylformamide, N,N-dimethylacetamide or N-methylpyrrolidin-2-one, optionally in the presence of a base such as an alkali or alkaline earth metal carbonate, alkoxide or hydroxide, for example sodium carbonate or potassium carbonate, or, such as, an organic amine base, for example, pyridine, 2,6-lutidine, collidine, 4-dimethylaminopyridine, triethylamine, morpholine or diazabicyclo-[5.4.0]undec-7-ene, and at a temperature in the range, for example, 0° to 50° C., conveniently at or near room temperature.

Anilines of the Formula (II) may be prepared according to the following scheme:

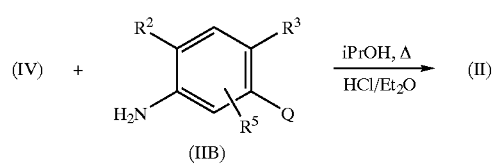

Q is —$NH_2$ or, if $R^2$ and $R^3$ are not identical and a stereospecific reaction is desired, Q can be amino protected by a suitable protecting group (such as those defined below) or nitro. After the above reaction, the protecting group is removed, or the nitro group is reduced (for example with iron powder and acetic acid) to generate an aniline of the Formula (II).

Activated heteroaryls of the Formula (IV) are known compounds, are commercially available or are prepared by processes known in the art. For example where L is chloro or pentafluorophenoxy, compounds of the Formula (IV) may be prepared by the following scheme:

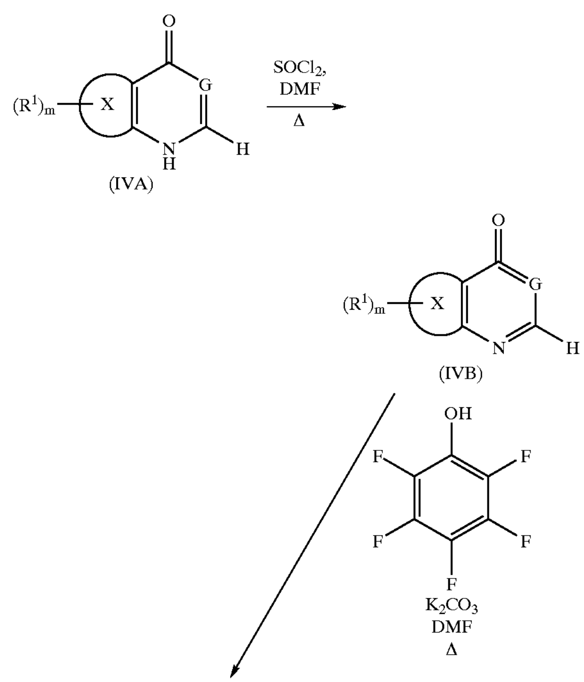

-continued (IVC)

For process variant b) A suitable displaceable group L is as defined above.

Activated heteroaryls of the formula (IV) and anilines of the Formula (V) may be reacted together in the presence of a protic solvent, for example, isopropanol, in the presence of an acid, for example hydrogen chloride gas in diethyl ether, or hydrochloric acid, and at a temperature in the range, for example, 0° to 150° C., conveniently at or near reflux.

Anilines of the Formula (V) are, known compounds, are commercially available, or are made by processes known in the art. For example, anilines of the Formula (V) may be prepared according to the following scheme:

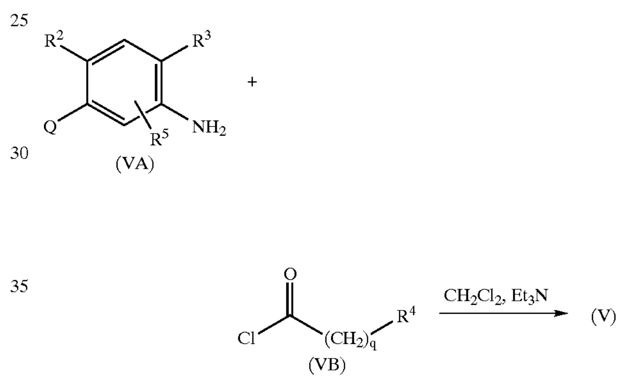

wherein Q is as defined above.

Compounds of the Formulae (IIB), (III), (VA) and (VB) are known compounds, are commercially available or are prepared by processes known in the art.

For process variant c) A suitable alkylating agent is, for example, any agent known in the art for the alkylation of hydroxy to alkoxy or substituted alkoxy, or for the alkylation of mercapto to alkylthio, or for the alkylation of amino to alkylamino or substituted alkylamino, for example an alkyl or substituted alkyl halide, for example a $C_{1-6}$alkyl chloride, bromide or iodide or a substituted $C_{1-6}$alkyl chloride, bromide or iodide, in the presence of a suitable base as defined below, in a suitable inert solvent or diluent as defined above for process variant a).

A suitable base is, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is conveniently carried out at a temperature in the range, for example, 10 to 150° C. preferably in the range 20 to 80° C.

Any necessary protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or arylaliphatic alcohol or of an ester-forming silanol (the said alcohol or silanol preferably containing 1–20 carbon atoms).

Examples of carboxy protecting groups include straight or branched chain $C_{1-12}$alkyl groups (for example isopropyl, tert-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); aryl lower alkyl groups (for example benzyl, p-methoxybenzyl, o-nitrobenzyl, p-nitrobenzyl, benzhydryl and phthalidyl); tri(lower alkyl) silyl groups (for example trimethylsilyl and tert-butyidimethylsilyl), tri(lower alkyl)silyl lower alkyl groups (for example trimethylsilylethyl); and $C_{2-6}$alkenyl groups (for example allyl and vinylethyl).

Methods particularly appropriate for the removal of carboxyl protecting groups include for example acid-, base-, metal- or enzymically-catalysed hydrolysis.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, tert-butyldimethylsilyl) and aryl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example tert-butoxycarbonyl); lower alkenyloxycarbonyl (for example allyloxycarbonyl); aryl lower alkoxycarbonyl groups (for example benzyloxycarbonyl, p-methoxybenzyloxycarbonyl, o-nitrobenzyloxycarbonyl, p-nitrobenzyloxycarbonyl; trialkylsilyl (for example trimethylsilyl and tert-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis for groups such as p-nitrobenzyloxycarbonyl, hydrogenation for groups such as benzyl and photolytically for groups such as o-nitrobenzyloxycarbonyl.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

According to a further aspect of the present invention there is provided a bicyclic compound of the Formula (I), or a pharmaceutically acceptable salt or an in vivo cleavable ester thereof as defined hereinbefore, for use in a method of treatment of the human or animal body by therapy.

In a further aspect of the present invention there is provided a bicyclic compound of the Formula (I), or a pharmaceutically acceptable salt or an in vivo cleavable ester thereof as defined hereinbefore, for use as a medicament.

In a further aspect the present invention provides the use of a bicyclic compound of the Formula (I), or a pharmaceutically acceptable salt or an in vivo cleavable ester thereof as defined hereinbefore, or the use of the compound 7-amino-4-(3-acetamidoanilino)pyrido[4,3-d]pyrimidine in the manufacture of a medicament for use in the treatment of diseases or medical conditions mediated by cytokines.

In a further aspect the present invention provides a method of treating diseases or medical conditions mediated by cytokines which comprises administering to a warm-blooded animal an effective amount of a bicyclic compound of the Formula (I), or a pharmaceutically acceptable salt or an in vivo cleavable ester thereof as defined hereinbefore, or of the compound 7-amino-4-(3-acetamidoanilino)pyrido[4,3-d]pyrimidine.

In a further aspect the present invention provides the use of a compound of the Formula (I), or a pharmaceutically acceptable salt or an in vivo cleavable ester thereof as defined hereinbefore, or the use of the compound 7-amino-4-(3-acetamidoanilino)pyrido[4,3-d]pyrimidine in the manufacture of a medicament for use in the treatment of diseases or medical conditions mediated by TNF, IL-1, IL-6 or IL-8.

In a further aspect the present invention provides a method of treating diseases or medical conditions mediated by TNF, IL-1, IL-6 or IL-8 which comprises administering to a warm-blooded animal an effective amount of a compound of the Formula (I), or a pharmaceutically acceptable salt or an in vivo cleavable ester thereof as defined hereinbefore, or of the compound 7-amino-4-(3-acetamidoanilino)pyrido[4,3-d]pyrimidine.

In a further aspect the present invention provides the use of a compound of the Formula (I), or a pharmaceutically acceptable salt or an in vivo cleavable ester thereof as defined hereinbefore, or the use of the compound 7-amino-4-(3-acetamidoanilino)pyrido[4,3-d]pyrimidine in the manufacture of a medicament for use in the treatment of diseases or medical conditions mediated by TNF.

In a further aspect the present invention provides a method of treating diseases or medical conditions mediated by TNF which comprises administering to a warm-blooded animal an effective amount of a compound of the Formula (I), or a pharmaceutically acceptable salt or an in vivo cleavable ester thereof as defined hereinbefore, or of the compound 7-amino-4-(3-acetamidoanilino)pyrido[4,3-d]pyrimidine.

In a further aspect the present invention provides the use of a compound of the Formula (I), or a pharmaceutically acceptable salt or an in vivo cleavable ester thereof as defined hereinbefore, or the use of the compound 7-amino-4-(3-acetamidoanilino)pyrido[4,3-a]pyrimidine in the manufacture of a medicament for use in inhibiting TNF, IL-1, IL-6 or IL-8.

In a further aspect the present invention provides a method of inhibiting TNF, IL-1, IL-6 or IL-8 which comprises administering to a warm-blooded animal an effective amount of a compound of the Formula (I), or a pharmaceutically acceptable salt or an in vivo cleavable ester thereof as defined hereinbefore, or of the compound 7-amino-4-(3-acetamidoanilino)pyrido[4,3-d]pyrimidine.

In a further aspect the present invention provides the use of a compound of the Formula (I), or a pharmaceutically acceptable salt or an in viva cleavable ester thereof as defined hereinbefore, or the use of the compound 7-amino-4-(3-acetamidoanilino)pyrido[4,3-d]pyrimidine in the manufacture of a medicament for use in inhibiting TNF.

In a further aspect the present invention provides a method of inhibiting TNF which comprises administering to a warm-blooded animal an effective amount of a compound of the Formula (I), or a pharmaceutically acceptable salt or an in vivo cleavable ester thereof as defined hereinbefore, or of the compound 7-amino-4-(3-acetamidoanilino)pyrido[4,3-d]pyrimidine.

In a further aspect the present invention provides the use of a compound of the Formula (I), or a pharmaceutically acceptable salt or an in vivo cleavable ester thereof as defined hereinbefore, or the use of the compound 7-amino-4-(3-acetamidoanilino)pyrido[4,3-d]pyrimidine in the manufacture of a medicament for use in the treatment of diseases or medical conditions mediated by p38 kinase.

In a further aspect the present invention provides a method of treating diseases or medical conditions mediated by p38 kinase which comprises administering to a warm-blooded animal an effective amount of a compound of the Formula (I), or a pharmaceutically acceptable salt or an in vivo cleavable ester thereof as defined hereinbefore, or of the compound 7-amino-4-(3-acetamidoanilino)pyrido[4,3-d]pyrimidine.

In a further aspect the present invention provides the use of a compound of the Formula (I), or a pharmaceutically acceptable salt or an in vivo cleavable ester thereof as defined hereinbefore, or the use of the compound 7-amino-4-(3-acetamidoanilino)pyrido[4,3-d]pyrimidine in the manufacture of a medicament for use in the production of a p38 kinase inhibitory effect.

In a further aspect the present invention provides a method of providing a p38 kinase inhibitory effect which comprises administering to a warm-blooded animal an effective amount of a compound of the Formula (I), or a pharmaceutically acceptable sail or an in vivo cleavable ester thereof as defined hereinbefore, or of the compound 7-amino-4-(3-acetamidoanilino)pyrido[4,3-d]pyrimidine.

In a further aspect the present invention provides the use of a compound of the Formula (I), or a pharmaceutically acceptable salt or an in vivo cleavable ester thereof as defined hereinbefore, or the use of the compound 7-amino-4-(3-acetamidoanilino)pyrido[4,3-d]pyrimidine in the manufacture of a medicament for use in the treatment of rheumatoid arthritis, asthma, irritable bowel disease, multiple sclerosis, AIDS, septic shock, ischaemic heart disease or psoriasis.

The following biological assays and Examples serve to illustrate the present invention.

Biological Assays

The following assays can be used to measure the p38 kinase-inhibitory, the TNF-inhibitory and anti-arthritic effects of the compounds of the present invention:

In vitro Enzyme Assay

The ability of compounds of the invention to inhibit the enzyme p38 kinase was assessed. Activity of particular test compounds against each of the p38α and p38β isoforms of the enzyme was determined.

Human recombinant MKK6 (GenBank Accesion Number G1209672) was isolated from Image clone 45578 (*Genomics*, 1996, 33, 151) and utilised to produce protein in the form of a GST fusion protein in a pGEX vector using analogous procedures to those disclosed by J. Han et al., *Journal of Biological Chemistry*, 1996, 271, 2886–2891. p38α (GenBank Accession Number G529039) and p38β (GenBank Accession Number G1469305) were isolated by PCR amplification of human lymphoblastoid cDNA (GenBank Accession Number GM1416) and human foetal brain cDNA [synthesised from mRNA (Clontech, catalogue no. 6525-1) using a Gibco superscript cDNA synthesis kit] respectively using oligonucleotides designed for the 5' and 3' ends of the human p38α and p38β genes using analogous procedures to those described by J. Han et al., *Biochimica et Biophysica Acta*, 1995, 126, 224–227 and Y. Jiang et al., *Journal of Biological Chemistry*, 1996, 271, 17920–17926.

Both p38 protein isoforms were expressed in *e coli* in PET vectors. Human recombinant p38α and p38β isoforms were produced as 5' c-myc, 6His tagged proteins. Both MKK6 and the p38 proteins were purified using standard protocols: the GST MKK6 was purified using a glutathione sepharose column and the p38 proteins were purified using nickel chelate columns.

The p38 enzymes were activated prior to use by incubation with MKK6 for 3 hours at 30° C. The unactivated coli-expressed MKK6 retained sufficient activity to fully activate both isoforms of p38. The activation incubate comprised p38α (10 μl of 10 mg/ml) or p38β (10 μl of 5 mg/ml) together with MKK6 (10 μl of 1 mg/ml), 'Kinase buffer' [100 μl; pH 7.4 buffer comprising Tris (50 mM), EGTA (0.1 mM), sodium orthovanadate (0.1 mM) and β-mercaptoethanol (0.1%)] and MgATP (30 μl of 50 mM $Mg(OCOCH_3)_2$ and 0.5 mM ATP). This produced enough activated p38 enzyme for 3 Microtiter plates.

Test compounds were solubilised in DMSO and 10 μl of a 1:10 diluted sample in 'Kinase Buffer' was added to a well in a Microtiter plate. For single dose testing, the compounds were tested at 10 μM. 'Kinase Assay Mix' [30 μl; comprising Myelin Basic Protein (Gibco BRL cat. no. 1322B-010; 1 ml of a 3.33 mg/ml solution in water), activated p38 enzyme (50 μl) and 'Kinase Buffer' (2 ml)] was then added followed by 'Labelled ATP' [10 μl, comprising 50 μM ATP, 0.1 μCi $^{33}P$ ATP (Amersham International cat. no. BF1000) and 50 mM $Mg(OCOCH_3)_2$]. The plates were incubated at room temperature with gentle agitation. Plates containing p38α were incubated for 90 min and plates containing p38β were incubated for 45 min. Incubation was stopped by the addition of 50 μl of 20% trichloroacetic acid (TCA). The precipitated protein was phosphorylated by p38 kinase and test compounds were assessed for their ability to inhibit this phosphorylation. The plates were filtered using a Canberra Packard Unifilter and washed with 2% TCA, dried overnight and counted on a Top Count scintillation counter.

Test compounds were tested initially at a single dose and active compounds were retested to allow $IC_{50}$ values to be determined.

In vitro Cell-based Assays (i) PBMC

The ability of compounds of this invention to inhibit TNFα production was assessed by using human peripheral blood mononuclear cells which synthesise and secrete TNFα when stimulated with lipopolysaccharide.

Peripheral blood mononuclear cells (PBMC) were isolated from heparinised (10 units/ml heparin) human blood by density centrifugation (Lymphoprep™; Nycomed). Mononuclear cells were resuspended in culture medium [RPMI 1640 medium (Gibco) supplemented with 50 units/ml penicillin, 50 μg/ml streptomycin, 2 mM glutamine and 1% heat-inactivated human AB serum (Sigma H-1513)]. Compounds were solubilised in DMSO at a concentration of 50 nM, diluted 1:100 in culture medium and subsequently serial dilutions were made in culture medium containing 1% DMSO. PBMCs ($2.4\times10^5$ cells in 160 μl culture medium) were incubated with 20 μl of varying concentrations of test compound (triplicate cultures) or 20 μl culture medium containing 1% DMSO (control wells) for 30 minutes at 37° C. in a humidified (5% $CO_2$/95% air) incubator (Falcon 3072; 96 well flat-bottom tissue culture plates). 20 μl lipopolysaccharide [LPS *E.Coli* 0111:B4 (Sigma L-4130), final concentration 10 μg/ml] solubilised in culture medium was added to appropriate wells. 20 μl culture medium was added to "medium alone" control wells. Six "LPS alone" and four "medium alone" controls were included on each 96 well plate. Varying concentrations of a known TNFα inhibitor were included in each test, i.e. an inhibitor of the PDE Type IV enzyme (for example see Semmler, J. Wachtel. H and Endres, S., *Int. J. Immunopharmac.* (1993), 15(3), 409–413) or an inhibitor of proTNFα convertase (for example, see McGeehan, G. M. et al. *Nature* (1994), 370, 558–561). Plates were incubated for 7 hours at 37° C. (humidified incubator) after which 100 μl of the supernatant was removed from each well and stored at −70° C. (96 well round-bottom plates; Corning 25850). TNFα levels were determined in each sample using a human TNFα ELISA (see WO92/10190 and *Current Protocols in Molecular Biology*, vol 2 by Frederick M. Ausbel et al., John Wiley and Sons Inc.).

$$\%\ \text{inhibition} = \frac{(LPS\ \text{alone} - \text{medium alone}) - (\text{test concentration} - \text{medium alone})}{(LPS\ \text{alone} - \text{medium alone})} \times 100$$

(ii) Human Whole Blood

The ability of the compounds of this invention to inhibit TNFα production was also assessed in a human whole blood assay. Human whole blood secretes TNFα when stimulated with LPS. This property of blood forms the basis of an assay which is used as a secondary test for compounds which profile as active in the PBMC test.

Heparinised (10 units/ml) human blood was obtained from volunteers. 160 μl whole blood were added to 96 well round-bottom plates (Corning 25850). Compounds were solubilised and serially diluted in RPMI 1640 medium (Gibco) supplemented with 50 units/ml penicillin, 50 μg/ml streptomycin and 2 mM glutamine, as detailed above. 20 μl of each test concentration was added to appropriate wells (triplicate cultures). 20 μl of RPMI 1640 medium supplemented with antibiotics and glutamine was added to control wells. Plates were incubated for 30 minutes at 37° C. (humidified incubator), prior to addition of 20 μl LPS (final concentration 10 μg/ml). RPMI 1640 medium was added to control wells. Six "LPS alone" and four "medium alone" controls were included on each plate. A known TNFα synthesis/secretion inhibitor was included in each test. Plates were incubated for 6 hours at 37° C. (humidified incubator). Plates were centrifuged (2000 rpm for 10 minutes) and 100 μl plasma removed and stored at −70° C. (Corning 25850 plates). TNFα levels were measured by ELISA (see WO92/10190 and *Current Protocols in Molecular Biology*, vol 2 by Frederick M. Ausbel et al., John Wiley and Sons Inc.). The paired antibodies that were used in the ELIZA were obtained from R&D Systems (catalogue nos. MAB610 anti-human TNFα coating antibody, BAF210 biotinylated anti-human TNFα detect antibody).

Ex vivo/In vivo Assessment

The ability of the compounds of this invention as ex vivo TNFα inhibitors were assessed in the rat or mouse. Briefly, groups of male Wistar Alderley Park (AP) rats (180–210 g) were dosed with compound (6 rats) or drug vehicle (10 rats) by the appropriate route, for example peroral (p.o.), intraperitoneal (i.p.) or subcutaneous (s.c.). Ninety minutes later rats were sacrificed using a rising concentration of $CO_2$ and bled out via the posterior vena cavae into 5 Units of sodium heparin/ml blood. Blood samples were immediately placed on ice and centrifuged at 2000 rpm for 10 min at 4° C. and the harvested plasmas frozen at −20° C. for subsequent assay of their effect on TNFα production by LPS-stimulated human blood. The rat plasma samples were thawed and 175 μl of each sample was added to a set format pattern in a 96 well round bottom plate (Corning 25850). 50 μl of heparinized human blood was then added to each well, mixed and the plate was incubated for 30 min at 37° C. (humidified incubator). LPS (25 μl; final concentration 10 μg/ml) was added to the wells and incubation continued for a further 5.5 hours. Control wells were incubated with 25 μl of medium alone. Plates were then centrifuged for 10 min at 2000 rpm and 200 μl of the supernatants were transferred to a 96 well plate and frozen at −20° C. for subsequent analysis of TNF concentration by ELISA.

Data analysis by dedicated software calculates for each compound/dose:

$$\%\ \text{inhibition of}\ TNF\alpha = \frac{\text{Mean}\ TNF\alpha\ (\text{Controls}) - \text{Mean}\ TNF\alpha\ (\text{Treated})}{\text{Mean}\ TNF\alpha\ (\text{Controls})} \times 100$$

Alternatively, mice could be used instead of rats in the above procedure.

Test as Anti-arthritic Agent

Activity of a compound as an anti-arthritic agent was tested as follows. Acid soluble native type II collagen was shown by Trentham et al. [1] to be arthritogenic in rats; it caused polyarthritis when administered in Freunds incomplete adjuvant. This is now known as collagen-induced arthritis (CIA) and similar conditions can be induced in mice and primates. Recent studies have shown that anti-TNF monoclonal antibodies [2] and TNF receptor-IgG fusion proteins [3] ameliorate established CIA indicating that TNF plays a key role in the pathophysiology of CIA. Moreover, the remarkable efficacy reported for anti-TNF monoclonal antibodies in recent rheumatoid arthritis clinical trials indicates that TNF plays a major role in this chronic inflammatory disease. Thus CIA in DBA/1 mice as described in references 2 and 3 is a tertiary model which can be used to demonstrate the anti-arthritic activity of a compound. Also see reference 4.

1. Trentham, D. E. et al., (1977) *J. Exp. Med.*, 146, 857.
2. Williams, R. O. et al., (1992) *Proc. Natl. Acad. Sci.*, 89, 9784.
3. Williams, R. O. et al., (1995) *Immunology*, 84, 433.
4 Badger, M. B. et al., (1996) *The Journal of Pharmacology and Experimental Therapeutics*, 279, 1453–1461.

Although the pharmacological properties of the compounds of the Formula (I) vary with structural change as expected, in general a compound of the Formula (I) gives over 30% inhibition of p38α and/or p38β at concentrations up to 10 μM and over 30% inhibition in the PBMC test at concentrations up to 50 μM. No physiologically unacceptable toxicity was observed at the effective dose for compounds tested of the present invention. By way of example:

| Example (Compound No.) | $IC_{50}$ (p38α) |
|---|---|
| 1 | 0.06 |
| 2 | 0.34 |
| 3(1) | 0.04 |
| 3(2) | 0.07 |

EXAMPLES

The invention will now be illustrated in the following non-limiting Examples in which, unless otherwise stated:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) was performed on Merck Kieselgel silica (Art. 9385) or Merck Lichroprep RP-18 (Art. 9303) reversed-phase silica obtained from E. Merck, Darmstadt, Germany;

(iv) yields where present are given for illustration only and are not necessarily the maximum attainable;

(v) in general, the end-products of the Formula (I) have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM250 spectrometer operating at a field strength of 250 MHz]; the following abbreviations have been used: s, singlet; d, doublet; t, triplet; m, multiplet; br, broad; unless otherwise stated deuterated dimethyl sulphoxide ($DMSO-d_0$) was the solvent used.

EXAMPLE 1

4-[2-Methyl-5-(2-morpholinopyridine-4-carboxamido)anilino]thieno[3,2-d]pyrimidine A mixture of N-(3-amino-4-methylphenyl)-2-morpholinopyridine-4-carboxamide (0.312 g), 4-chlorothieno[3,2-d]pyrimidine (PCT Patent Application WO 95/19774; 0.171 g), triethylamine (0.15 ml) and N,N-dimethylformamide (5 ml) was stirred and heated to 120° C. for 36 h. The mixture was cooled to ambient temperature and poured into water. The resultant precipitate was isolated and purified by column chromatography on silica using a 19:1 mixture of ethyl acetate and methanol as eluent. There was thus obtained the title compound as a solid (0.216 g, 48%); NMR: 2.14 (s, 3H), 3.51 (m, 4H), 3.69 (m, 4H), 7.08 (d, 1H), 7.21 (s, 1H), 7.29 (d, 1H), 7.37 (d, 1H), 7.68 (d, 1H), 7.74 (s, 1H), 8.08 (d, 1H), 8.26 (d, 1H), 8.43 (s, 1H), 9.48 (s, 1H), 10.29 (s, 1H); Mass: $M+H^+$ 447.

The N-(3-amino-4-methylphenyl)-2-morpholinopyridine-4-carboxamide used as a starting material was obtained as follows:

Triethylamine (31.8 ml) was added to a stirred mixture of 4-methyl-3-nitroaniline (15.8 g), 2-chloropyridine-4-carbonyl chloride (20 g) and methylene chloride (1 liter) and the resultant mixture was stirred at ambient temperature for 16 hours. The precipitate was isolated, washed with a saturated aqueous sodium bicarbonate solution and with methylene chloride and dried under vacuum at 40° C. There was thus obtained 2-chloro-N-(4-methyl-3-nitrophenyl) pyridine-4-carboxamide (10.2 g). The organic filtrate was washed with a saturated aqueous sodium bicarbonate solution, dried ($MgSO_4$) and evaporated. The residue was triturated under methylene chloride and the resultant solid was isolated and dried under vacuum at 40° C. There was thus obtained a second crop (8.13 g) of 2-chloro-N-(4-methyl-3-nitrophenyl)pyridine-4-carboxamide; NMR: 2.48 (s, 3H), 7.51 (d, 1H), 7.86 (m, 1H), 7.96 (m, 2H), 8.49 (m, 1H), 8.64 (m, 1H), 10.85 (s, 1H); Mass: $M+H^+$ 292 and 294.

A mixture of the pyridine-4-carboxamide so produced and morpholine (250 ml) was stirred and heated to 100° C. for 18 hours. The mixture was poured into water (250 ml) and stirred for 10 minutes. Methylene chloride (30 ml) was added and the resultant mixture was stirred for 30 minutes. The resultant solid was isolated, washed with methylene chloride and dried in a vacuum oven at 40° C. for 18 hours. There was thus obtained N-(4-methyl-3-nitrophenyl)-2-morpholinopyridine-4-carboxamide (17.34 g); NMR: 2.48 (s, 3H), 3.52 (m, 4H), 3.71 (m, 4H), 7.1 (d, 1H), 7.25 (s, 1H), 7.49 (d, 1H) 7.97 (m, 1H), 8.29 (m, 1H), 8.49 (m, 1H), 10.62 (s, 1H); Mass: $M+H^+$ 343.

A mixture of a portion (8.5 g) of the material so obtained, 5% palladium-on-carbon catalyst (0.85 g) and methanol (600 ml) was stirred under an atmosphere pressure of hydrogen gas for 18 hours. Methylene chloride (400 ml) was added and the reaction mixture was filtered through diatomaceous earth. The filtrate was evaporated to give N-(3-amino-4-methylphenyl)-2-morpholinopyridine-4-carboxamide (6.41 g); NMR: 2.01 (s, 3H), 3.52 (m, 4H), 3.73 (m, 4H), 4.83 (s, 2H), 6.78 (d, 1H), 6.84 (d, 1H) 7.04–7.08 (m, 2H), 7.2 (s, 1H), 8.24 (d, 1H), 9.95 (s, 1H); Mass: $M+H^+$ 313.

EXAMPLE 2

4-[2-Methyl-5-(2-morpholinopyridine-4-carboxamido)anilino]-5-methylthieno[2,3-d]pyrimidine A 1M solution of hydrogen chloride in diethyl ether (0.2 ml) was added to a mixture of N-(3-amino-4-methylphenyl)-2-morpholinopyridine-4-carboxamide (0.056 g), 4-chloro-5-methylthieno[2,3-d]pyrimidine (Maybridge Chemical Company, Trevillet, Tintagel, Cornwall, PL34 0HW, GB; 0.037 g) and isopropanol (2 ml) and the reaction mixture was stirred and heated to 88° C. for 18 hours. The reaction mixture was cooled to ambient temperature and the precipitate was isolated and washed in turn with isohexane and diethyl ether. There was thus obtained the title compound (0.021 g); Mass: $M+H^+$ 461.

EXAMPLE 3

Using an analogous procedure to that described in Example 2, the appropriate 4-chloroheterocycle (obtained, unless otherwise stated from Maybridge Chemical Company, Trevillet, Tintagel, Cornwall, PL34 0HW, GB) was reacted with the appropriate aniline to give the compounds described in the following table.

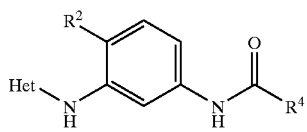

| No. | Het | $R^2$ | $R^4$ | Note |
|---|---|---|---|---|
| 1 | 7-methylthieno[3,2-d]pyrimidin-4-yl | Me | 2-morpholinopyrid-4-yl | a) |
| 2 | thieno[2,3-d]pyrimidin-4-yl | Me | 2-morpholinopyrid-4-yl | b) |
| 3 | 2-methylthiothiazolo[5,4-d]pyrimidin-7-yl | Me | 2-morpholinopyrid-4-yl | c) |
| 4 | pyrido[4,3-d]pyrimidin-4-yl | Me | 2-morpholinopyrid-4-yl | d) |
| 5 | pyrido[2,3-d]pyrimidin-4-yl | Me | 2-morpholinopyrid-4-yl | e) |
| 6 | pteridin-4-yl | Me | 2-morpholinopyrid-4-yl | f) |
| 7 | 6-purinyl | Me | 2-morpholinopyrid-4-yl | g) |

Notes a) The product gave the following data: Mass: $M + H^+$ 461.

b) The 4-chlorothieno[2,3-d]pyrimidine used as a starting material was obtained as described in PCT Patent Application WO 95/19774 The product gave the following data: Mass: $M + H^+$ 447.

c) The product gave the following data: Mass: $M + H^+$ 494.

d) The product gave the following data: Mass: $M + H^+$ 442. The 4-chloropyrido[4,3-d]pyrimidine used as a starting material was obtained as follows: A mixture of pyrido[4,3-d]pyrimidin-4(1H)-one (PCT Patent Application WO 95/19774; 0.03 g) and thionyl chloride (2 ml) was stirred and heated to reflux for 4 h. The reaction mixture was cooled to ambient temperature and evaporated to give the required starting material which was used without further purification.

e) The product gave the following data: Mass: $M + H^+$ 442. The 4-chloropyrido[2,3-d]pyrimidine used as a starting material was obtained as follows: A mixture of pyrido[2,3-d]pyrimidin-4(1H)-one (PCT Patent Application WO 95/19774; 0.03 g) and thionyl chloride (2 ml) was stirred and heated to reflux for 4 h. The reaction mixture was cooled to ambient temperature and evaporated to give the required starting material which was used without further purification.

f) The product gave the following data: Mass: $M + H^-$ 443.

g) The product gave the following data: NMR: 2.18(s, 3H), 3.52(m, 4H), 3.75(m, 4H), 7.09(m, 1H), 7.22(m, 2H), 7.55(m, 1H), 7.84(broad s, 1H), 8.18(broad s, 1H), 8.24(m, 2H), 9.14(broad s, 1H), 10.26(s, 1H); Mass: $M + H^+$ 431.

EXAMPLE 4

Pharmaceutical Compositions

The following illustrate representative pharmaceutical dosage forms of the invention as defined herein (the active ingredient being termed "Compound X"), for therapeutic or prophylactic use in humans:

| | mg/tablet |
|---|---|
| (a) Tablet I | |
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b) Tablet II | |

-continued

| | |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium | 1.5 |

| (e) Injection I | (50 mg/ml) |
|---|---|
| Compound X | 5.0% w/v |
| 1M Sodium hydroxide solution | 15.0% v/v |
| 0.1M Hydrochloric acid | (to adjust pH to 7.6) |
| Polyethylene glycol 400 | 4.5% w/v |
| Water for injection | to 100% |

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection | to 100% |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

| | mg/ml |
|---|---|
| (h) Aerosol I | |
| Compound X | 10.0 |
| Sorbitan trioleate | 13.5 |
| Trichlorofluoromethane | 910.0 |
| Dichlorodifluoromethane | 490.0 |
| (i) Aerosol II | |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound X | 40 mg |
| Ethanol | 300 μl |
| Water | 300 μl |

-continued

| | |
|---|---|
| 1-Dodecylazacycloheptan-2-one | 50 μl |
| Propylene glycol | to 1 ml |

Note
The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:

1. A bicyclic compound of the Formula (I):

(I)

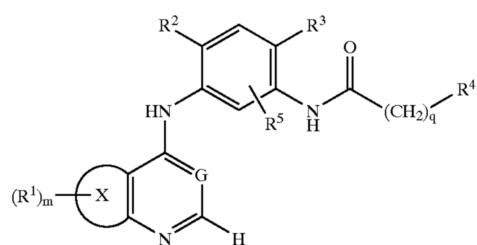

wherein:

G is N;

the bicyclic ring formed by the fusion of ring X to the adjacent nitrogen-containing 6-membered heteroaryl ring within Formula (I) is furopyrimidinyl, thienopyrimidinyl, pyrrolopyrimidinyl, oxazolopyrimidinyl, thiazolopyrimidinyl, purinyl, pyridopyrimidinyl, pyrimidopyrimidinyl or pteridinyl;

m is 0 or 1;

$R^1$ is hydroxy, halo, $C_{1-6}$alkyl, $C_{1-6}$alkoxy, $C_{1-6}$alkylS(O)$_n$— (wherein n is 0–2), N,N-($C_{1-6}$alkyl)$_2$amino$C_{1-6}$ alkyl, N,N-($C_{1-6}$alkyl)$_2$carbamoyl$C_{1-6}$alkoxy, N,N-($C_{1-6}$alkyl)$_2$amino$C_{1-6}$alkoxy, $C_{1-6}$alkylS(O)$_2$—$C_{1-6}$ alkoxy, N,N-($C_{1-6}$alkyl)$_2$amino-N-($C_{1-6}$alkyl)$C_{1-6}$ alkylamino, N,N-($C_{1-6}$alkyl)$_2$amino$C_{1-6}$ alkylamino$C_{1-6}$alkyl, piperidin-1-yl$C_{1-6}$alkyl, homopiperidin-1-yl$C_{1-6}$alkyl, N-($C_{1-6}$alkyl)piperidin-1-yl$C_{1-6}$alkyl, N-($C_{1-6}$alkyl) homopiperidin-1-yl$C_{1-6}$ alkyl, piperazin-1-yl$C_{1-6}$alkyl, 4-$C_{1-6}$alkylpiperazin-1-yl$C_{1-6}$alkyl, homopiperazinyl-1-yl$C_{1-6}$alkyl, 4-$C_{1-6}$ alkylhomopiperazinyl-1-yl$C_{1-6}$alkyl, pyrrolidinyl$C_{1-6}$ alkoxy, piperidinyl$C_{1-6}$alkoxy, homopiperidinyl$C_{1-6}$ alkoxy, N-($C_{1-6}$alkyl)pyrrolidinyl$C_{1-6}$alkoxy, N-($C_{1-6}$ alkyl)piperidinyl$C_{1-6}$alkoxy, N-($C_{1-6}$alkyl) homopiperidinyl$C_{1-6}$alkoxy, morpholinyl$C_{1-6}$alkoxy, piperazinyl$C_{1-6}$alkoxy, N-($C_{1-6}$alkyl)piperazinyl$C_{1-6}$ alkoxy, homopiperazinyl$C_{1-6}$alkoxy, N-($C_{1-6}$alkyl) homopiperazinyl$C_{1-6}$alkoxy, pyrrolidinyloxy, N-$_{1-6}$ alkyl)pyrrolidinyloxy, piperidinyloxy, N-($C_{1-6}$alkyl) piperidinyloxy, homopiperidinyloxy, N-($C_{1-6}$alkyl) homopiperidinyloxy, morpholinyl$C_{1-6}$alkylamino$C_{1-6}$ alkyl, thiazolyl$C_{1-6}$alkoxy or pyridyl$C_{1-6}$alkoxy;

and any aryl, heteroaryl or heterocyclyl group in a $R^1$ group may be optionally substituted with one or more groups selected from hydroxy, halo, $C_{1-6}$alkyl, $C_{1-6}$alkoxy, carboxy, $C_{1-6}$alkoxycarbonyl, carbamoyl, N-$C_{1-6}$alkylcarbamoyl, N-($C_{1-6}$alkyl)$_2$ carbamoyl, $C_{2-6}$alkanoyl, amino, N-$C_{1-6}$alkylamino and N,N-($C_{1-6}$ alkyl)$_2$amino, and any heterocyclyl group in a $R^1$ group may be optionally substituted with one or two oxo or thioxo substituents, and any of the $R^1$ groups defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, $C_{1-6}$alkoxy, N-$C_{1-6}$alkylamino, N,N-($C_{1-6}$alkyl)$_2$amino and heterocyclyl;

$R^2$ is hydrogen, $C_{1-4}$alkyl or halo;

$R^3$ is hydrogen, $C_{1-4}$alkyl or halo;

q is 0;

$R^4$ is phenyl, thienyl, furyl, oxazolyl, isoxazolyl, pyrimidyl or pyridyl optionally substituted by one or two halo, trifluoromethyl, cyano, $C_{1-4}$alkyl, $C_{1-4}$alkoxy, —O—($C_{1-3}$alkyl)—O—, N,N-($C_{1-4}$alkyl)$_2$amino, $C_{1-6}$alkanoylamino, $C_{1-6}$alkylsulphonyl-N-($C_{1-6}$alkyl) amino, phenyl (optionally substituted by one or two halo groups), furyl, azetidinyl, pyrrolidinyl, 3-pyrrolinyl, piperidinyl, homopiperidinyl, morpholino, piperazinyl, homopiperazinyl, N-($C_{1-6}$ alkyl)piperazinyl and N-($C_{1-6}$alkyl)homopiperazinyl, or $R^4$ is fluorenyl or dibenzofuranyl;

and any aryl, heteroaryl or heterocyclyl group in a $R^4$ group may be optionally substituted by one or more groups selected from hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O—($C_{1-3}$alkyl)—O—, $C_{1-6}$alkylS(O)$_n$— (wherein n is 0–2), N-$C_{1-6}$ alkylamino, N,N-($C_{1-6}$alkyl)$_2$amino, $C_{1-6}$alkoxycarbonyl, N-$C_{1-6}$alkylcarbamoyl, N,N-($C_{1-6}$ alkylcarbamoyl, $C_{2-6}$alkanoyl, $C_{1-6}$alkanoyloxy, $C_{1-6}$alkanoylamino, N-$C_{1-6}$alkylsulphamoyl, N,N-($C_{1-6}$ alkyl)$_2$sulphamoyl, $C_{1-6}$alkylsulphonylamino and $C_{1-6}$alkylsulphonyl-N-($C_{1-6}$alkyl)amino, or any aryl, heteroaryl or heterocyclyl group in a $R^4$ group may be optionally substituted with one or more groups of the Formula (IA'):

$$—B^1—(CH_2)_p—A^1 \qquad (IA')$$

wherein $A^1$ is halo, hydroxy, $C_{1-6}$alkoxy, cyano, amino, N-$C_{1-6}$alkylamino, N,N-($C_{1-6}$alkyl)$_2$amino, carboxy, $C_{1-6}$alkoxycarbonyl, carbamoyl, N-$C_{1-6}$ alkylcarbamoyl or N,N-($C_{1-6}$alkyl)$_2$carbamoyl, p is 1–6, and $B^1$ is a bond, oxy, imino, N-($C_{1-6}$alkyl)imino or —NHC(O)—, with the proviso that p is 2 or more unless $B^1$ is a bond or —NHC(O)—, or any aryl, heteroaryl or heterocyclyl group in a $R^4$ group may be optionally substituted with one or more groups of the Formula (IB'):

$$—E^1—D^1 \qquad (IB')$$

wherein $D^1$ is aryl, heteroaryl or heterocyclyl and $E^1$ is a bond, $C_{1-6}$alkylene, oxy$C_{1-6}$alkylene, oxy, imino, N-($C_{1-6}$alkyl)imino, imino$C_{1-6}$alkylene, N-($C_{1-6}$alkyl) imino$C_{1-6}$alkylene, $C_{1-6}$alkylene-oxy$C_{1-6}$alkylene, $C_{1-6}$alkylene-imino$C_{1-6}$alkylene, $C_{1-6}$alkylene-N-($C_{1-6}$ alkyl)-imino$C_{1-6}$alkylene, —NHC(O)—, —NHSO$_2$—, —SO$_2$NH— or —NHC(O)-$C_{1-6}$alkylene-, and any aryl, heteroaryl or heterocyclyl group in a substituent on $R^4$ may be optionally substituted with one or more groups selected from hydroxy, halo, $C_{1-6}$alkyl, $C_{1-6}$alkoxy, carboxy, $C_{1-6}$alkoxycarbonyl, carbamoyl, N-$C_{1-6}$alkylcarbamoyl, N-($C_{1-6}$alkyl)$_2$carbamoyl, $C_{2-6}$alkanoyl, amino, N-$C_{1-6}$alkylamino and N,N-($C_{1-6}$ alkyl)$_2$amino, and any $C_{3-7}$cycloalkyl or heterocyclyl group in a $R^4$ group may be optionally substituted with one or two oxo or thioxo substituents, and any of the $R^4$ groups defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, $C_{1-6}$alkoxy, N-$C_{1-6}$alkylamino, N,N-($C_{1-6}$alkyl)$_2$amino and heterocyclyl;

and $R^5$ is hydrogen;

or a pharmaceutically acceptable salt or an in vivo cleavable ester thereof.

2. A bicyclic compound of the Formula (I) according to claim 1 wherein:

$R^1$ is hydroxy, halo, $C_{1-6}$alkyl, $C_{1-6}$alkoxy, $C_{1-6}$alkylS(O)$_n$— (wherein n is 0–2), N,N-($C_{1-6}$alkyl)$_2$amino$C_{1-6}$ alkyl, N,N-($C_{1-6}$alkyl)$_2$carbamoyl$C_{1-6}$alkoxy, N,N-($C_{1-6}$alkyl)$_2$amino$C_{1-6}$alkoxy, $C_{1-6}$alkylS(O)$_2$—$C_{1-6}$ alkoxy, N,N-($C_{1-6}$alkyl)$_2$amino-N-($C_{1-6}$alkyl)$C_{1-6}$ alkylamino, N,N-($C_{1-6}$alkyl)$_2$amino$C_{1-6}$ alkylamino$C_{1-6}$alkyl, piperazin-1-yl$C_{1-6}$alkyl, 4-$C_{1-6}$ alkylpiperazin-1-yl$C_{1-6}$alkyl, homopiperazinyl-1-yl$C_{1-6}$alkyl, 4-$C_{1-6}$alkylhomopiperazinyl-1-yl$C_{1-6}$ alkyl, pyrrolidinyl$C_{1-6}$alkoxy, piperidinyl$C_{1-6}$alkoxy, N-($C_{1-6}$alkyl)pyrrolidinyl$C_{1-6}$alkoxy, N-($C_{1-6}$alkyl) piperidinyl$C_{1-6}$alkoxy, morpholinyl$C_{1-6}$alkoxy, piperazinyl$C_{1-6}$alkoxy, N-($C_{1-6}$alkyl)piperazinyl$C_{1-6}$ alkoxy, homopiperazinyl$C_{1-6}$alkoxy, N-($C_{1-6}$alkyl) homopiperazinyl$C_{1-6}$alkoxy, pyrrolidinyloxy, piperidinyloxy, morpholinyl$C_{1-6}$alkylamino$C_{1-6}$alkyl or pyridyl$C_{1-6}$alkoxy; and $R^4$ is phenyl, thienyl, furyl, oxazolyl, isoxazolyl, pyrimidyl or pyridyl optionally substituted by one or two halo, cyano, $C_{1-4}$alkyl, $C_{1-4}$alkoxy, N,N-($C_{1-4}$alkyl)$_2$ amino, piperidinyl, morpholino or piperazinyl;

or a pharmaceutically acceptable salt or an in vivo cleavable ester thereof.

3. A bicyclic compound of the Formula (I) according to claim 1 wherein:

the bicyclic ring formed by the fusion of ring X to the adjacent nitrogen-containing 6-membered heteroaryl ring within Formula (I) is furo[3,2-d]pyrimidinyl, furo[2,3-d]pyrimidinyl, thieno[3,2-d]pyrimidinyl, thieno[2,3-d]pyrimidinyl, pyrrolo[3,2-d]pyrimidinyl, pyrrolo[2,3-d]pyrimidinyl, oxazolo[5,4-d]pyrimidinyl, oxazolo[4,5-d]pyrimidinyl, thiazolo[5,4-d]pyrimidinyl, thiazolo[4,5-d]pyrimidinyl, purinyl, pyrido[2,3-d]pyrimidinyl, pyrido[3,4-d]pyrimidinyl, pyrido[4,3-d]pyrimidinyl, pyrido[3,2-d]pyrimidinyl, pyrimido[4,5-d]pyrimidinyl, pyrimido[5,6-d]pyrimidinyl or pteridinyl;

$R^1$ is methyl, methoxy, methylthio, 2-diisopropylaminoethoxy, 3-diethylaminopropoxy, 3-morpholinopropoxy or 3-pyrrolidin-1-ylpropoxy;

$R^2$ is hydrogen, methyl, fluoro or chloro;

$R^3$ is hydrogen; and $R^4$ is phenyl optionally substituted by one or two groups selected from fluoro, chloro, trifluoromethyl, cyano, methyl, methoxy, ethoxy, methylenedioxy, N,N-dimethylamino, acetamido, N-methylmethanesulphonamido, phenyl, 4-fluorophenyl, 4-chlorophenyl, 2-furyl, azetidin-1-yl, pyrrolidin-1-yl, 3-pyrrolin-1-yl, piperidino, homopiperidin-1-yl, morpholino, piperazin-1-yl, homopiperazin-1-yl, 4-methylpiperazin-1-yl and 4-methylhomopiperazin-1-yl, or $R^4$ is pyridyl optionally substituted by a N,N-dimethylamino, N,N-diethylamino, azetidin-1-yl, pyrrolidin-1-yl, 3-pyrrolin-1-yl, piperidino, homopiperidin-1-yl, morpholino, piperazin-1-yl, homopiperazin-1-yl, 4-methylpiperazin-1-yl or 4-methylhomopiperazin-1-yl group, or $R^4$ is 1-fluorenyl or dibenzofuran-4-yl;

or a pharmaceutically acceptable salt or an in vivo cleavable ester thereof.

4. A bicyclic compound of the Formula (I) according to claim 1 wherein:

the bicyclic ring formed by the fusion of ring X to the adjacent nitrogen-containing 6-membered heteroaryl ring within Formula (I) is furo[3,2-d]pyrimidinyl, furo[2,3-d]pyrimidinyl, thieno[3,2-d]pyrimidinyl, thieno[2,3-d]pyrimidinyl, pyrrolo[3,2-d]pyrimidinyl, pyrrolo[2,3-d]pyrimidinyl, oxazolo[5,4-d]pyrimidinyl, oxazolo[4,5-d]pyrimidinyl, thiazolo[5,4-d]pyrimidinyl, thiazolo[4,5-d]pyrimidinyl, purinyl, pyrido[2,3-d]pyrimidinyl, pyrido[3,4-d]pyrimidinyl, pyrido[4,3-d]pyrimidinyl, pyrido[3,2-d]pyrimidinyl, pyrimido[4,5-d]pyrimidinyl, pyrimido[5,6-d]pyrimidinyl or pteridinyl;

$R^1$ is methyl, methoxy, methylthio, 2-diisopropylaminoethoxy, 3-diethylaminopropoxy, 3-morpholinopropoxy or 3-pyrrolidin-1-ylpropoxy;

$R^2$ is hydrogen, methyl, fluoro or chloro;

$R^3$ is hydrogen; and $R^4$ is pyridyl optionally substituted by a N,N-dimethylamino, N,N-diethylamino, pyrrolidin-1-yl, piperidino or morpholino group;

or a pharmaceutically acceptable salt or an in vivo cleavable ester thereof.

5. A bicyclic compound of the Formula (I) according to claim 1 wherein:

the bicyclic ring formed by the fusion of ring X to the adjacent nitrogen-containing 6-membered heteroaryl ring within Formula (I) is thieno[3,2-d]pyrimidin-4-yl, thieno[2,3-d]pyrimidin-4-yl, thiazolo[5,4-d]pyrimidin-7-yl, 6-purinyl, pyrido[2,3-d]pyrimidin-4-yl, pyrido[3,4-d]pyrimidin-4-yl, pyrido[4,3-d]pyrimidin-4-yl, pyrido[3,2-d]pyrimidin-4-yl or pteridin-4-yl;

$R^1$ is methyl or methylthio;

$R^2$ is methyl;

$R^3$ is hydrogen; and $R^4$ is phenyl, 3-fluorophenyl, 4-cyanophenyl, 2-methylphenyl, 2-methoxyphenyl, 3-methoxyphenyl, 3-ethoxyphenyl, 3,4-dimethoxyphenyl, 3,4-methylenedioxyphenyl, 3-(N,N-dimethylamino) phenyl, 3-acetamidophenyl, 3-(4-fluorophenyl)phenyl, 3-(2-furyl)phenyl, 3-pyrrolidin-1-ylphenyl, 3-morpholinophenyl, 3-fluoro-5-pyrrolidin-1-ylphenyl, 3-fluoro-5-piperidinophenyl, 3-fluoro-5-morpholinophenyl or 3-morpholino-5-trifluoromethylphenyl, or $R^4$ is 2-morpholinopyrid-4-yl, or $R^4$ is 1-fluorenyl or dibenzofuran-4-yl;

or a pharmaceutically acceptable salt or an in vivo cleavable ester thereof.

6. A bicyclic compound of the Formula (I) according to claim 1 wherein:

the bicyclic ring formed by the fusion of ring X to the adjacent nitrogen-containing 6-membered heteroaryl ring within Formula (I) is thieno[3,2-d]pyrimidin-4-yl, thieno[2,3-d]pyrimidin-4-yl, thiazolo[5,4-d]pyrimidin-7-yl, pyrido[2,3-d]pyrimidin-4-yl, pyrido[3,4-d]pyrimidin-4-yl, pyrido[4,3-d]pyrimidin-4-yl, pyrido[3,2-d]pyrimidin-4-yl or pteridin-4-yl;

$R^1$ is methyl or methylthio;

$R^2$ is methyl;

$R^3$ is hydrogen; and $R^4$ is 2-morpholinopyrid-4-yl;

or a pharmaceutically acceptable salt or an in vivo cleavable ester thereof.

7. A bicyclic compound of the Formula (I) according to claim 1 selected from:

4-[2-methyl-5-(2-morpholinopyridine-4-carboxamido)anilino]thieno[3,2-d]pyrimidine, 4-[2-methyl-5-(2-morpholinopyridine-4-carboxamido)anilino]pyrido[4,3-d]pyrimidine, 4-[2-methyl-5-(2-morpholinopyridine-4-carboxamido)anilino]pteridine and 6-[2-methyl-5-(2-morpholinopyridine-4-carboxamido)anilino]purine;

or a pharmaceutically acceptable salt or an in vivo cleavable ester thereof.

8. A process for preparing a compound of the Formula (I), or a pharmaceutically acceptable salt or an in vivo cleavable ester thereof, according to claim 1 which comprises:

a) reacting an aniline of the Formula (II):

(II)

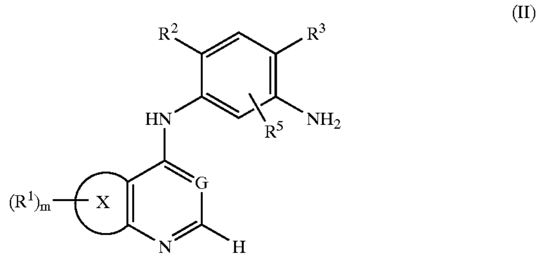

with an acyl compound of the Formula (III):

(III)

$$L-C(=O)-(CH_2)_q-R^4$$

wherein G, $R^1$, $R^2$, $R^3$, $R^4$, $R^5$, m, q and the bicyclic ring formed by the fusion of ring X to the adjacent nitrogen-containing 6-membered heteroaryl ring are as defined in claim 2 and L is a displaceable group;

b) reacting an activated bicyclic heteroaryl ring of the Formula (IV):

(IV)

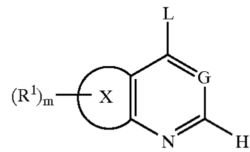

wherein G, $R^1$, m and the bicyclic ring formed by the fusion of ring X to the adjacent nitrogen-containing 6-membered heteroaryl ring are as defined in claim 2 and wherein L is a displaceable group, with an aniline of the Formula (V):

(V)

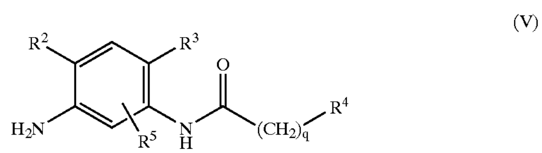

wherein $R^2$, $R^3$, $R^4$, $R^5$ and q are as defined in claim 2; or c) for the preparation of a compound of the Formula (I) wherein $R^1$ or a substituent on $R^4$ is $C_{1-6}$alkoxy or substituted $C_{1-6}$alkoxy, $C_{1-6}$alkylS—, N-$C_{1-6}$alkylamino, N,N-$(C_{1-6}alkyl)_2$amino, the alkylation, conveniently in the presence of a suitable base, of a compound of the Formula (I) wherein $R^1$ or a substituent on $R^4$ is hydroxy, mercapto or amino as appropriate;

and thereafter if necessary:

i) converting a compound of the Formula (I) into another compound of the Formula (I);

ii) removing any protecting groups; and iii) forming a pharmaceutically acceptable salt or in vivo cleavable ester.

9. A pharmaceutical composition which comprises a bicyclic compound of the Formula (I), or a pharmaceutically acceptable salt or in vivo cleavable ester thereof, according to any one of claims 1–7 in association with a pharmaceutically acceptable diluent or carrier.

10. A method of treating a disease or medical condition mediated by cytokines which comprises administering to a warm-blooded animal in need thereof an effective amount of a bicyclic compound of the Formula (I), or a pharmaceutically acceptable salt or an in vivo cleavable ester thereof, according to any one of claims 1–7.

11. A method for producing an enzyme p38 kinase inhibiting effect in a warm-blooded animal which comprises administering to said animal an enzyme inhibiting amount of a compound of Formula (I), or a pharmaceutically acceptable salt or an in vivo cleavable ester thereof, according to any one of claims 1–7.

12. A method for producing a TNFα inhibiting effect in a warm-blooded animal which comprises administering to said animal a TNFα inhibiting amount of a compound of Formula (I), or a pharmaceutically acceptable salt or an in vivo cleavable ester thereof, according to any one of claims 1–7.

13. A method for the treatment of rheumatoid arthritis in a warm-blooded animal in need thereof comprising administering to said animal a treatment-effective amount of a compound of Formula (I), or a pharmaceutically acceptable salt or an in vivo cleavable ester thereof, according to any one of claims 1–7.

* * * * *